United States Patent [19]
Yoon

[11] Patent Number: 5,366,459
[45] Date of Patent: Nov. 22, 1994

[54] SURGICAL CLIP AND CLIP APPLICATION PROCEDURES

[75] Inventor: Inbae Yoon, 2101 Highland Ridge Dr., Phoenix, Md. 21131

[21] Appl. No.: 719,281

[22] Filed: Sep. 18, 1991

Related U.S. Application Data

[60] Division of Ser. No. 450,301, Dec. 15, 1989, Pat. No. 5,100,418, which is a continuation-in-part of Ser. No. 49,504, May 14, 1987, abandoned, and Ser. No. 515,641, Apr. 2, 1990, Pat. No. 5,171,250, which is a continuation of Ser. No. 49,526, May 14, 1989, abandoned.

[51] Int. Cl.$^5$ ............................................. A61B 17/00
[52] U.S. Cl. .................................... 606/151; 606/157
[58] Field of Search ........................... 606/151–158; 24/543, 545, 23 W, 546

[56] References Cited

U.S. PATENT DOCUMENTS

| | | | |
|---|---|---|---|
| 3,874,042 | 4/1975 | Eddleman et al. | 606/157 |
| 4,414,721 | 11/1983 | Hufnagel | 606/158 |
| 4,449,531 | 5/1984 | Cerwin et al. | 606/158 |
| 4,476,865 | 10/1984 | Failla et al. | 606/158 |
| 4,686,983 | 8/1987 | Leisman et al. | 606/158 |
| 5,062,846 | 11/1991 | Oh et al. | |

FOREIGN PATENT DOCUMENTS 1364322  1/1988  U.S.S.R. ...................... 606/151

*Primary Examiner*—Stephen C. Pellegrino
*Assistant Examiner*—Gary Jackson

[57] ABSTRACT

A variety of configurations for suture tie devices and suture tie device applicators, as well as methods of suturing, are disclosed. The suture tie devices generally include at least one leg member having a curved or angled distal, tissue engaging portion. A tying member unidirectionally or bidirectionally displaceable along the leg member can optionally be provided. Engagement of a leg distal portion with a generally opposed leg distal portion or the tying member forms a suture loop which positions organ or tissue material between the curved or angled legs and the tying member. The tying member can be advanced toward the leg member so as to provide a variable extent of suture tension. Apparatus for installing the suture tie devices and suturing methods are also disclosed.

20 Claims, 15 Drawing Sheets

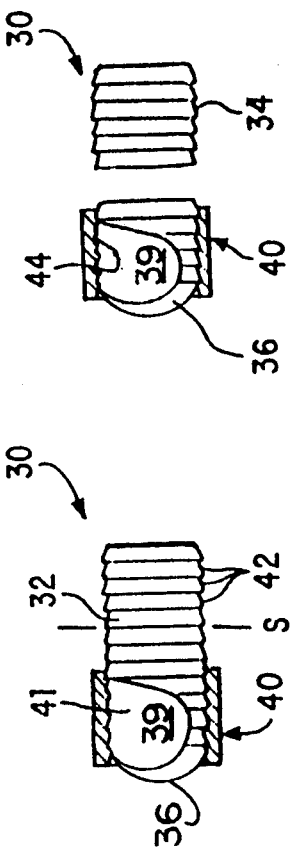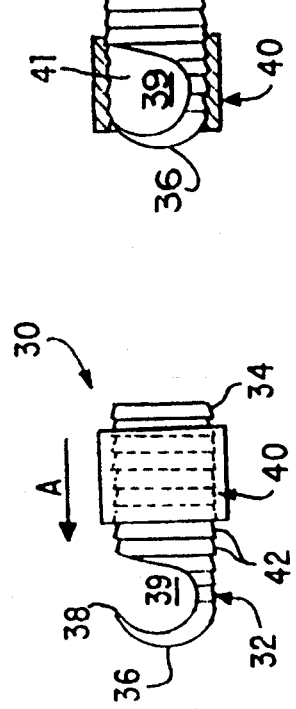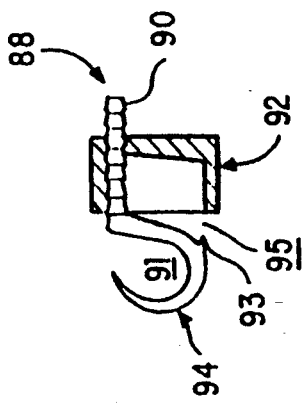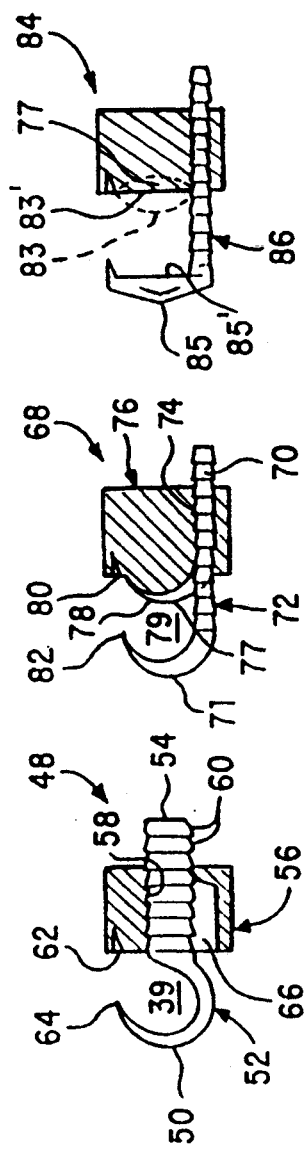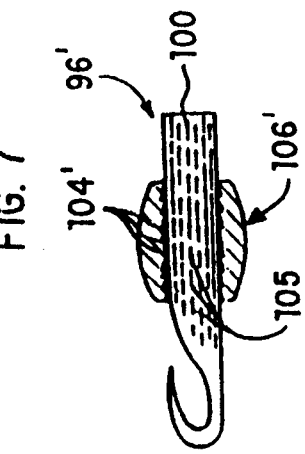

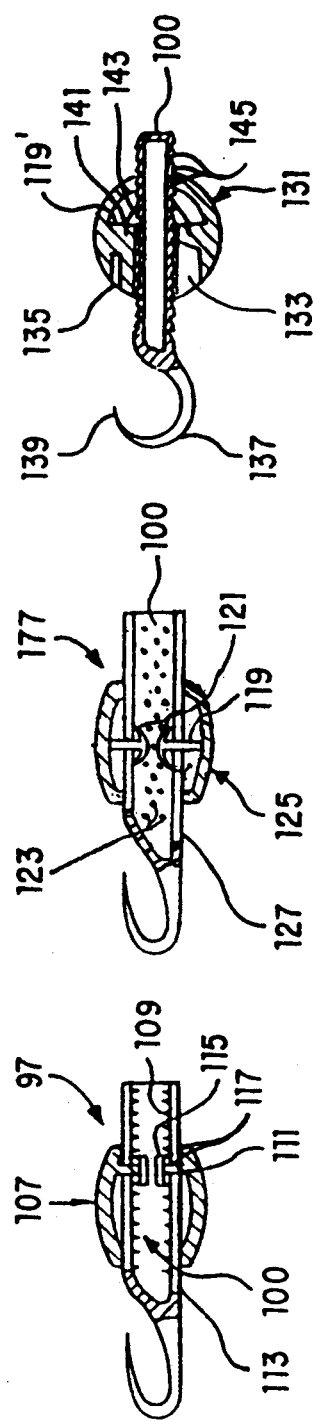
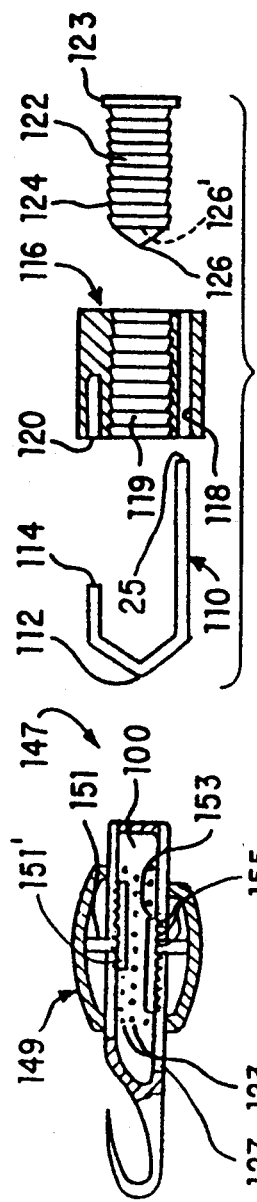
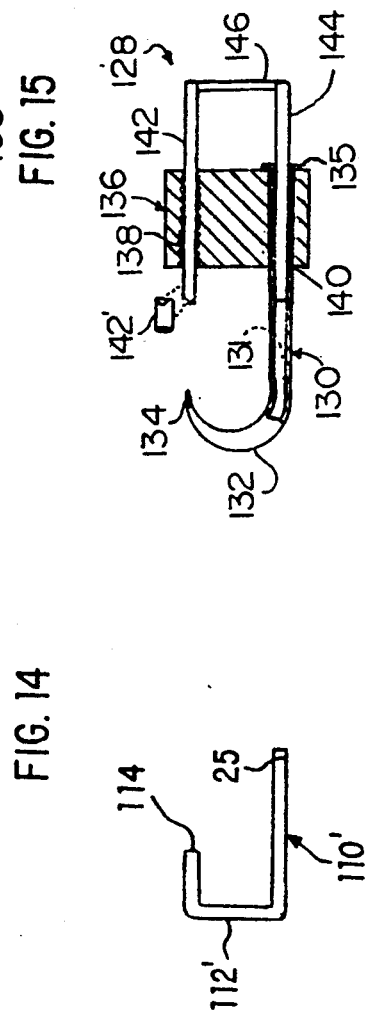
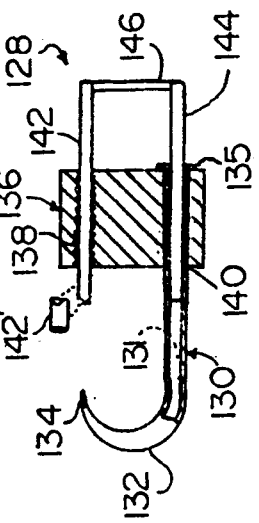
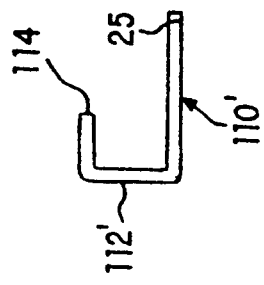

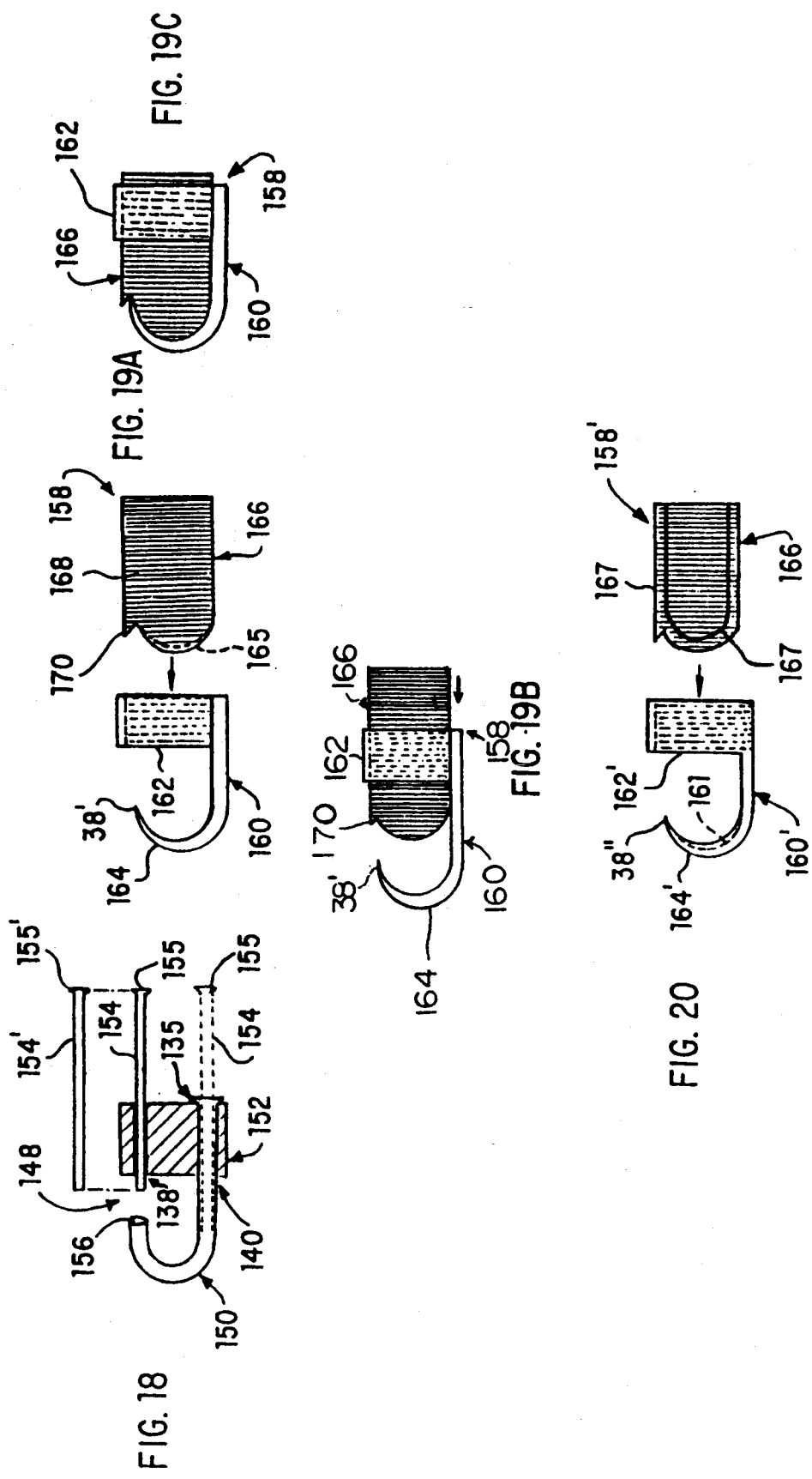

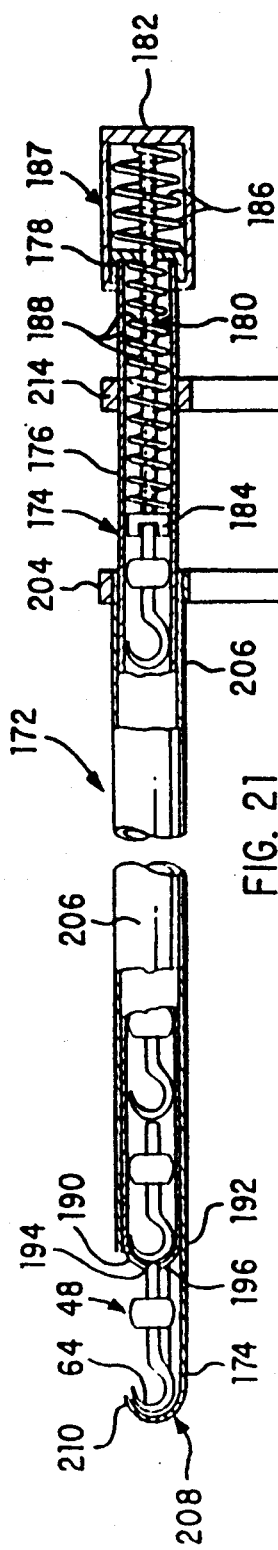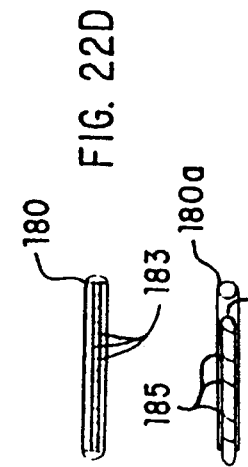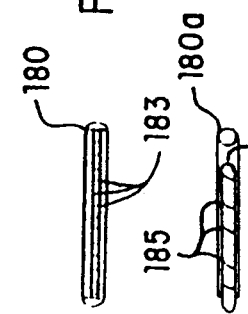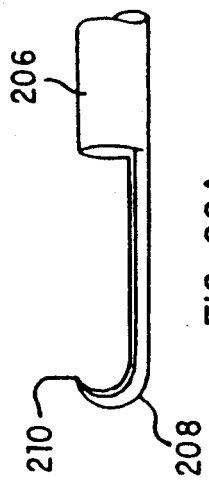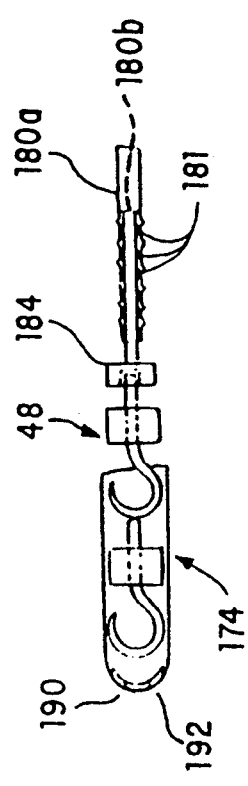

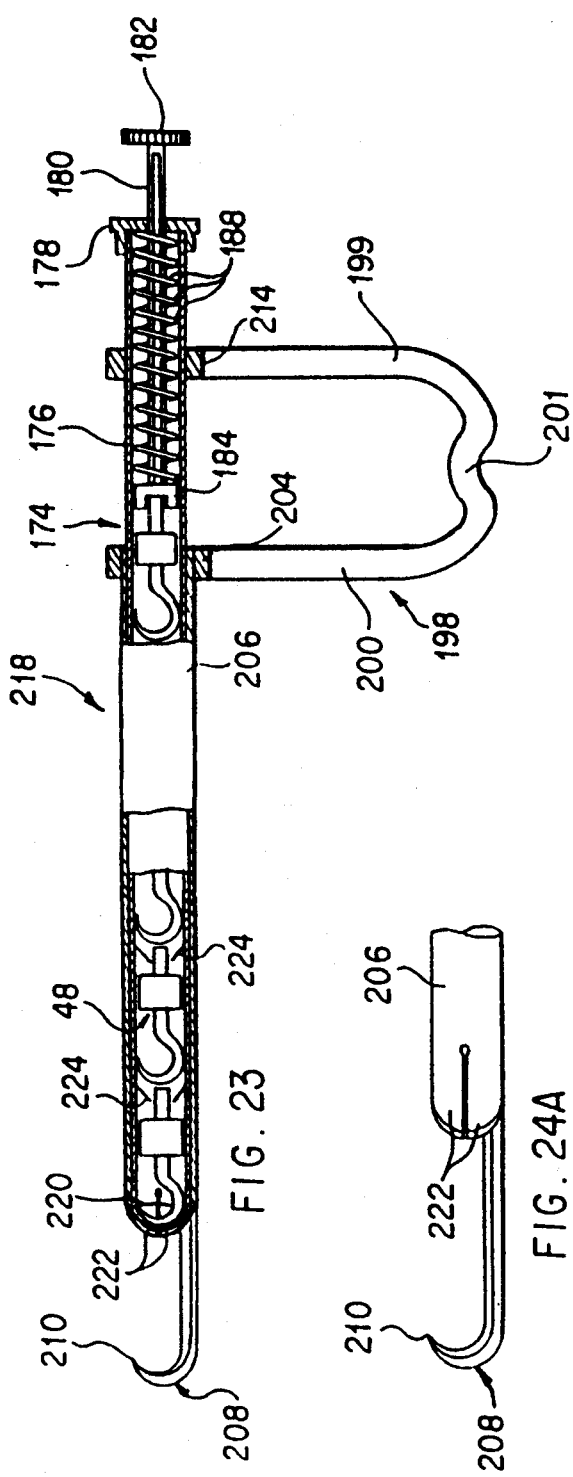
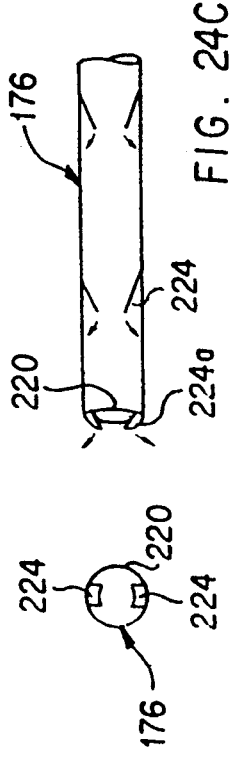

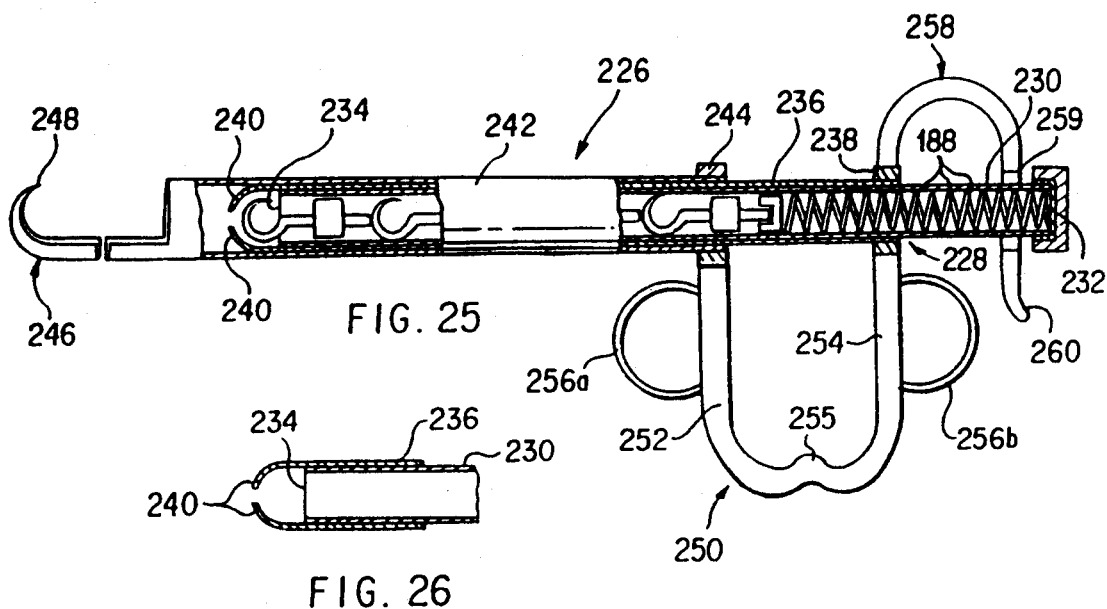
FIG. 25
FIG. 26
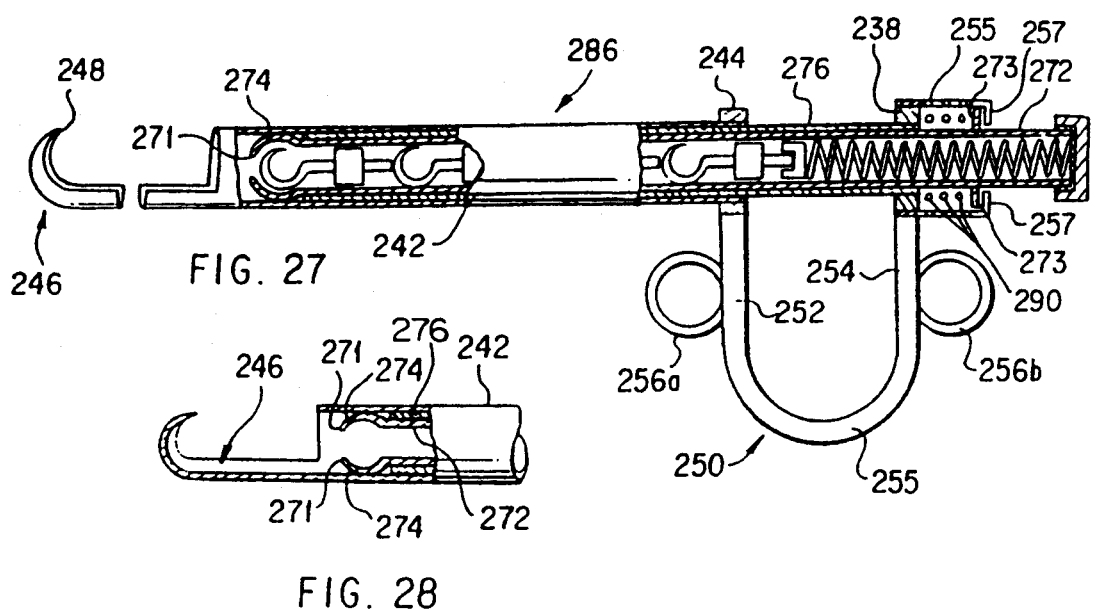
FIG. 27
FIG. 28

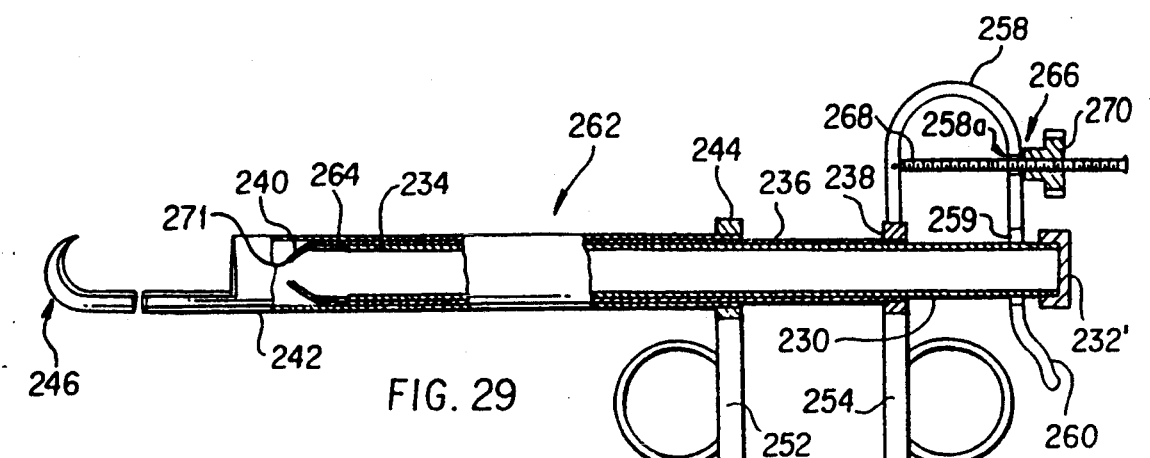
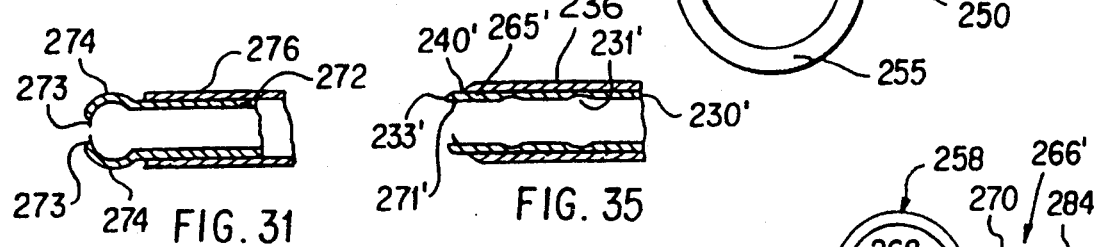
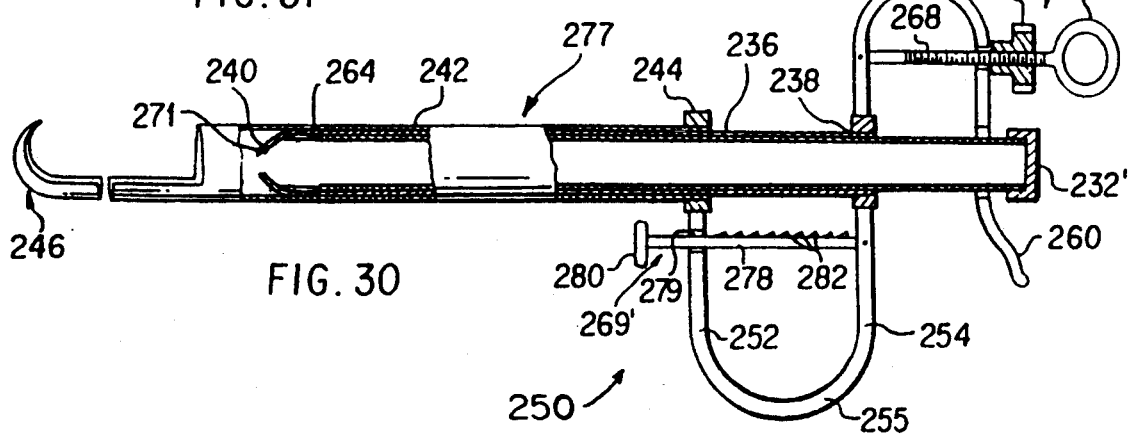
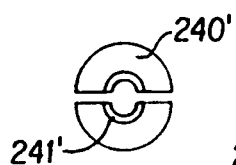 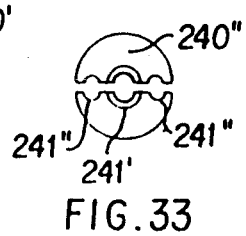 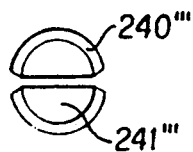

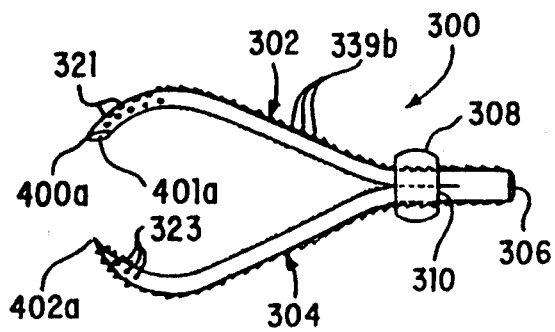
FIG. 36A
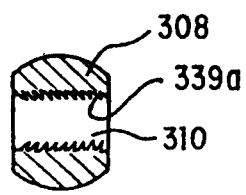
FIG. 36B
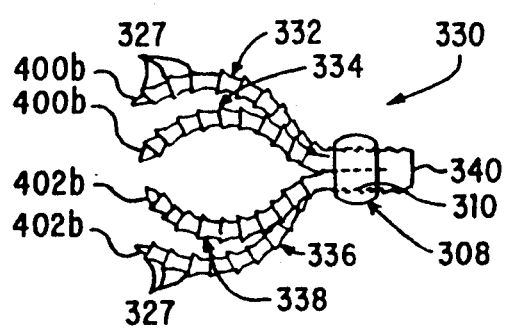
FIG. 37
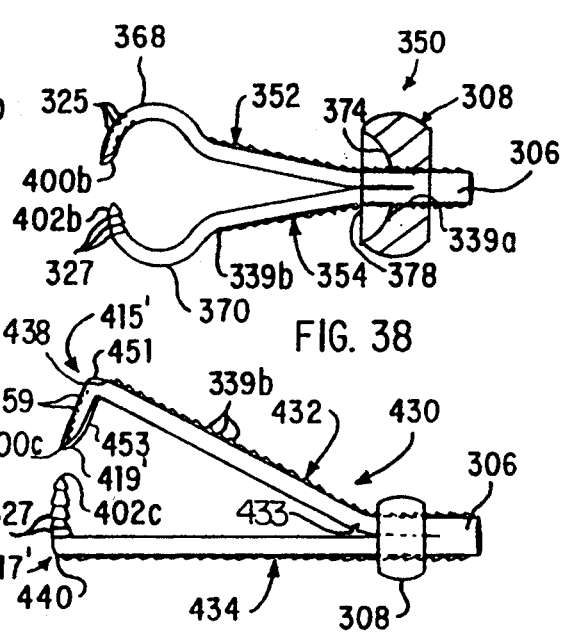
FIG. 38
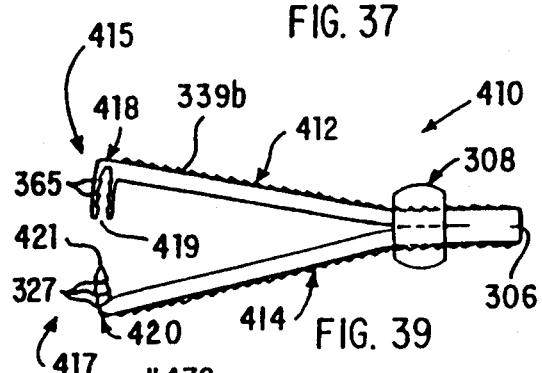
FIG. 39
FIG. 40
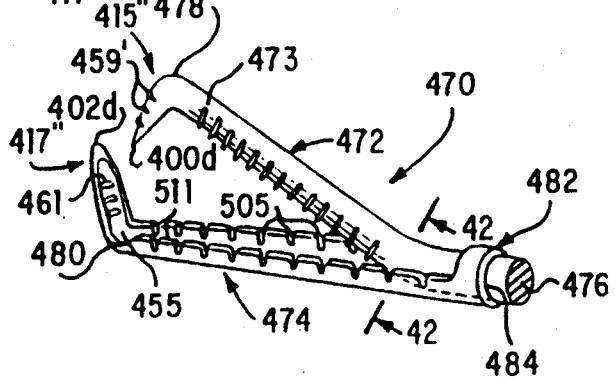
FIG. 41
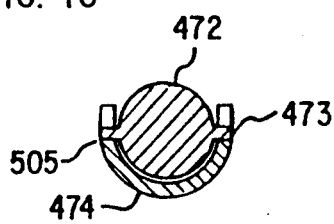
FIG. 42

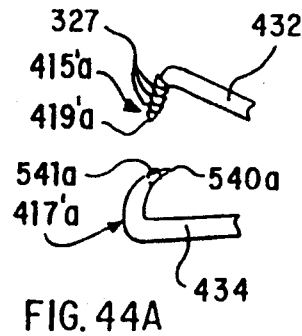
FIG. 44A
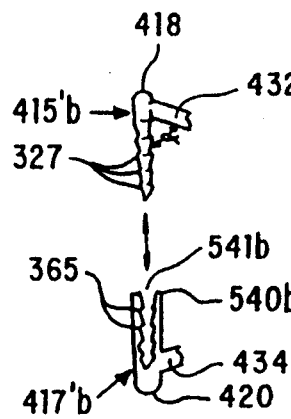
FIG. 44B
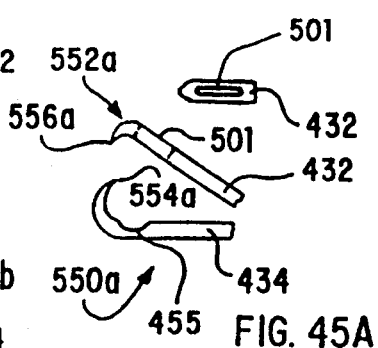
FIG. 45A / FIG. 45B
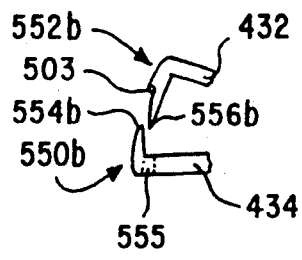
FIG. 45C
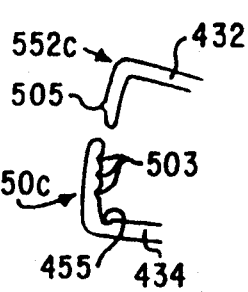
FIG. 45D
FIG. 46
FIG. 47
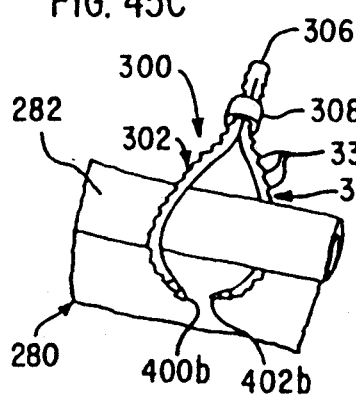
FIG. 48A
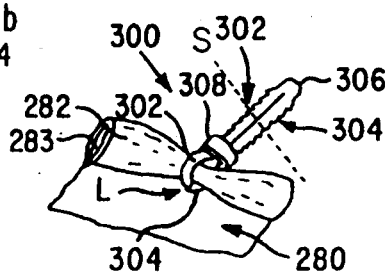
FIG. 48B
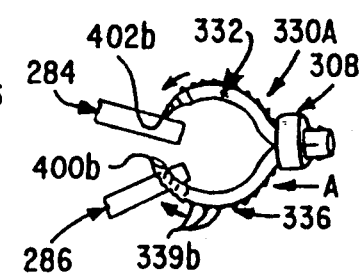
FIG. 49A
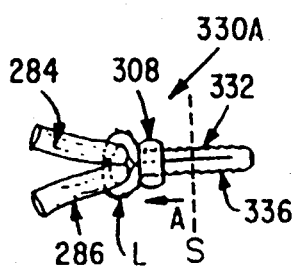
FIG. 49B
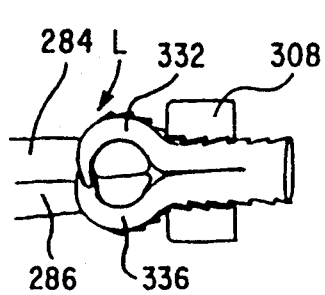
FIG. 49C
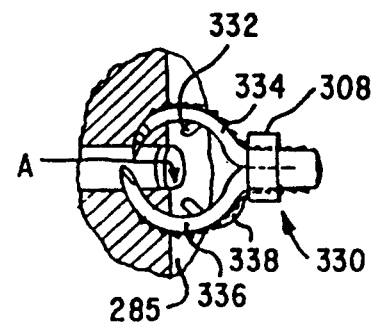
FIG. 50

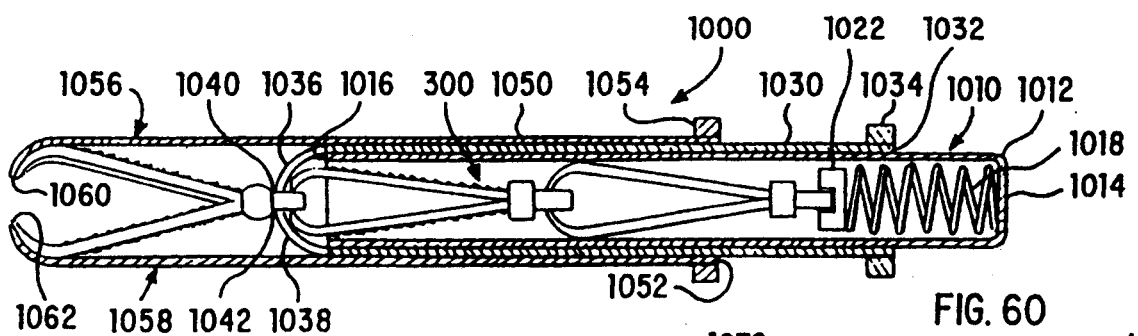
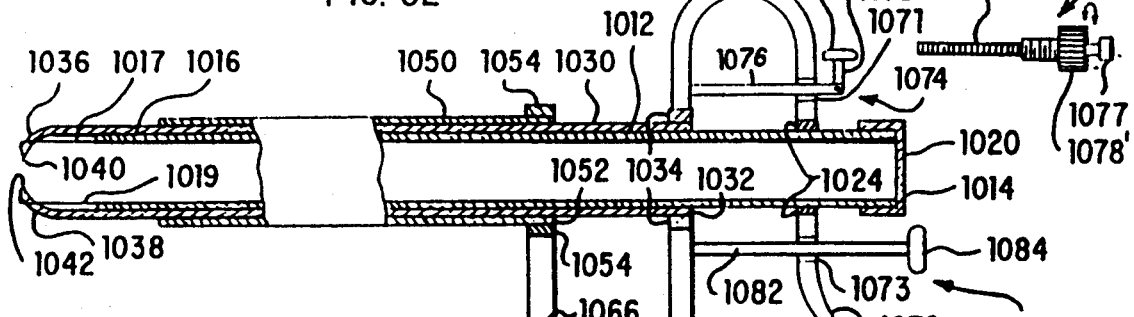
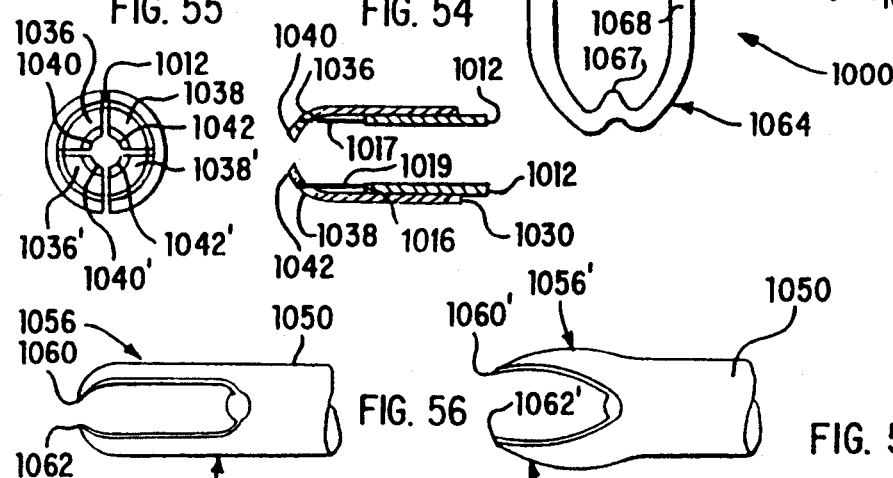
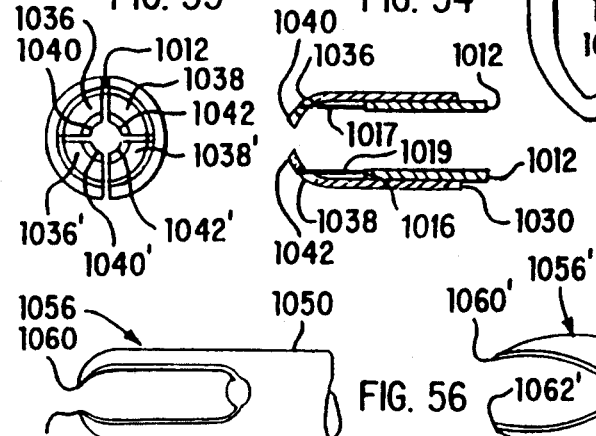
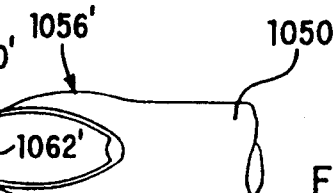
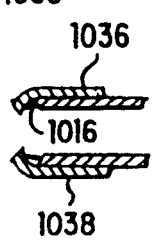
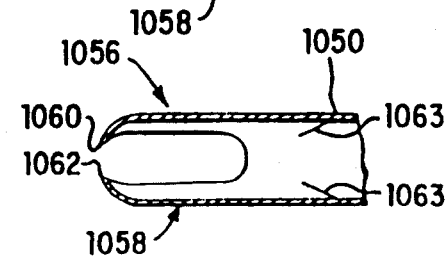

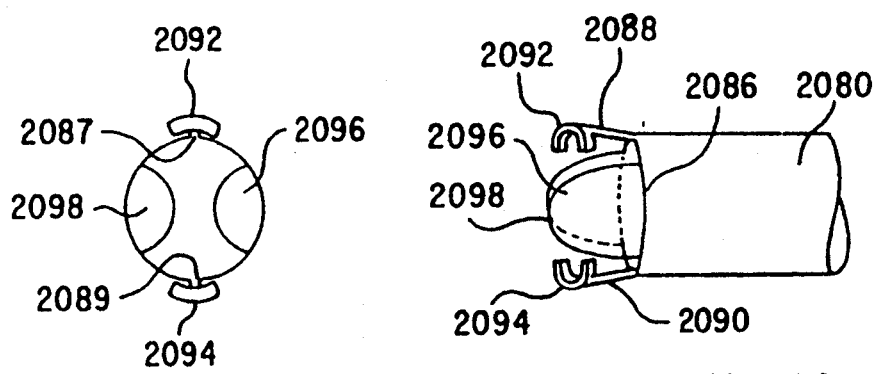
FIG. 68B
FIG. 68A
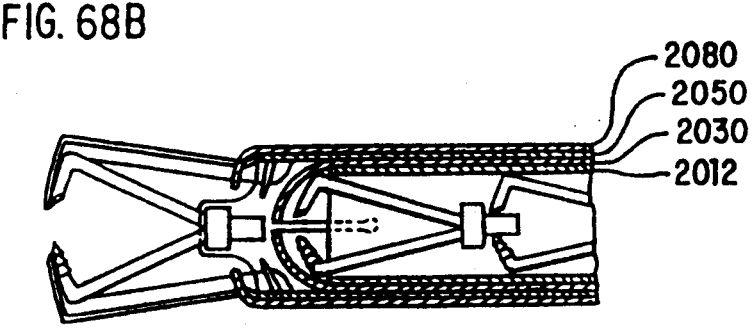
FIG. 69

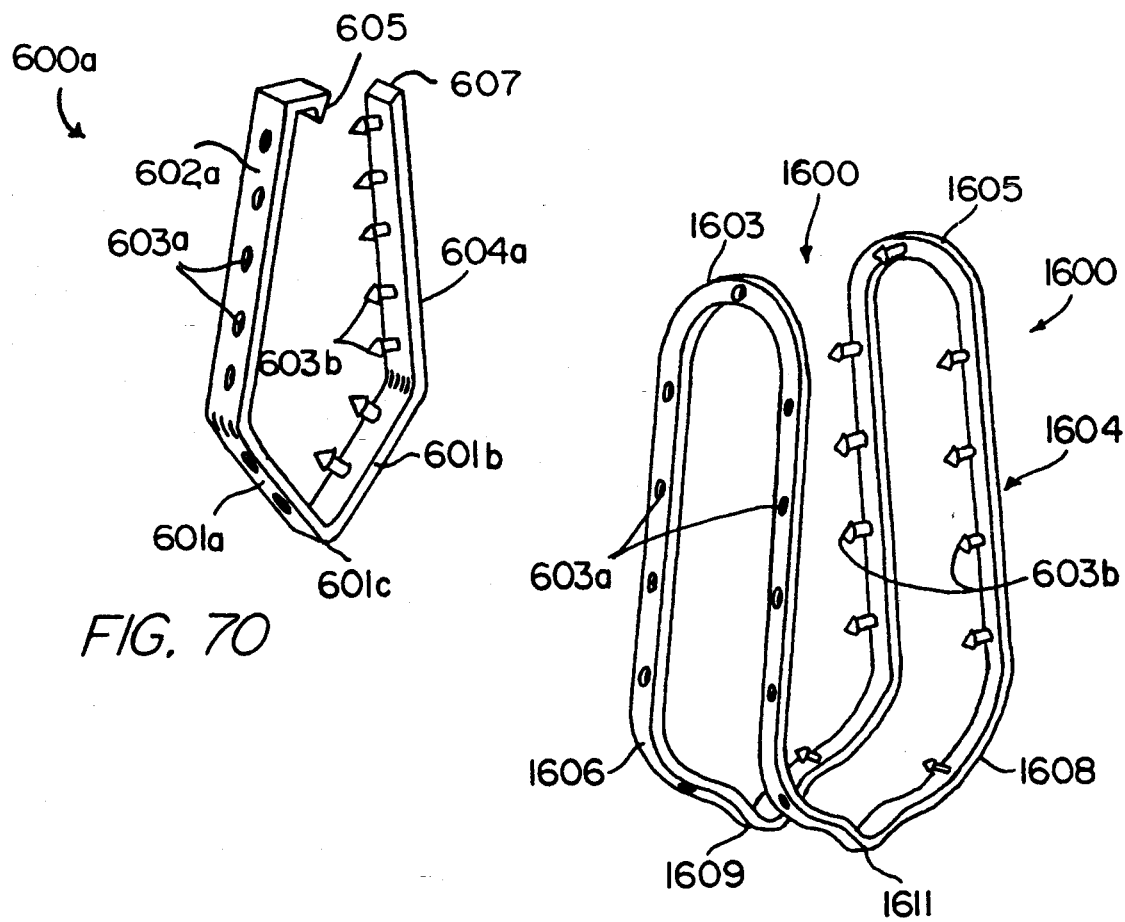
FIG. 70
FIG. 72
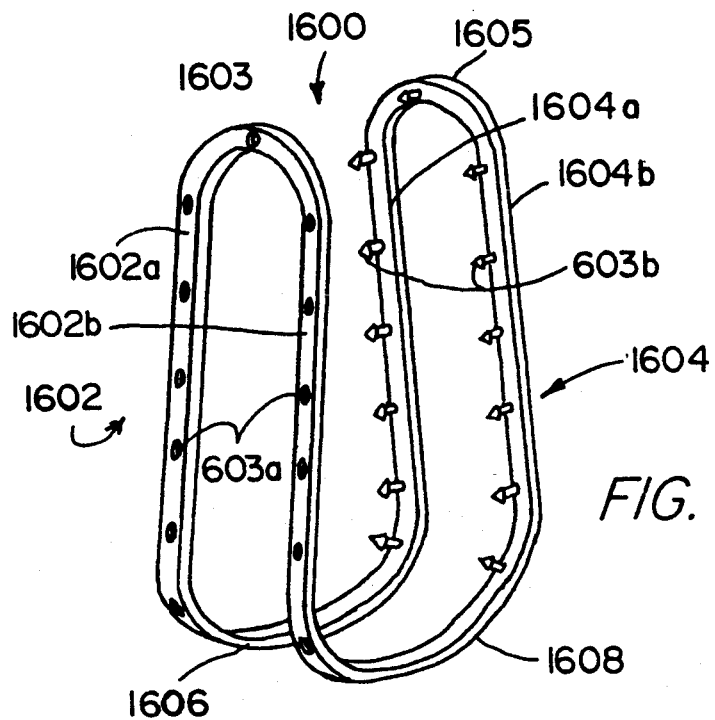
FIG. 71

SURGICAL CLIP AND CLIP APPLICATION PROCEDURES

This application is a divisional of patent application Ser. No. 450,301 filed on Dec. 15, 1989, issued as U.S. Pat. No. 5,100,418 on Mar. 31, 1992, and which is a continuation-in-part of Ser. No. 049,504 filed on May 14, 1987 (now abandoned), and Ser. No. 515,641 filed on Apr. 2, 1990, now U.S. Pat. No. 5,171,250 which is a continuation of Ser. No. 049,526 filed on May 14, 1987 (now abandoned).

BACKGROUND OF THE INVENTION

1. Field of the Invention

The present invention relates generally to surgical suturing apparatus and suturing procedures and, more particularly, to suture tie devices preferably and advantageously made of bioabsorbable materials that are particularly useful in endoscopic surgery, applicators for such suture tie devices, and methods of suturing using such suture tie devices.

2. Discussion of the Related Art

Suturing of bodily tissue is a time consuming part of most surgical procedures, including both open surgery and endoscopic or closed surgery. As used throughout this disclosure, the term "open" surgery relates to surgery wherein the surgeon gains access to the surgical site by way of a relatively large incision formed in the outer surface of the patient's body, whereas the terms "endoscopic" and "closed" surgery relate to surgery wherein the surgeon gains access to the surgical site by way of one or more relatively small portals formed in the outer surface of the patient's body through which one or more surgical instruments can be introduced to the surgical site. A variety of instruments, such as endoscopes, forceps, cutters, and applicators and the like, can be introduced through the portals to the surgical site. Commonly performed endoscopic surgical procedures include arthroscopy, laparoscopy (pelviscopy), gastroentroscopy, and laryngobronchoscopy.

Prior to the development of the subject suture device, suturing had been accomplished through the use of a sharp, curved metal suture needle attached to the end of a length of thread-like suture material. The surgeon or surgical attendant would extend the suture needle and trailing suture material through the tissue to be joined by the suture, after which the suture material would be tied into a knot and manipulated such that the knot could be advanced to the tissue site and adjusted for tension in order to accommodate the particular type of tissue being sutured and to control and account for approximation, occlusion, attachment, and other conditions of the tissue. The ability to control tension is extremely important to the surgeon regardless of the type of surgical procedure being performed; however, knotting of the suture material is time consuming and tedious work, particularly in microsurgery and endoscopic surgery. For example, suturing during microsurgery procedures is necessarily tedious and time consuming due to the reduced-size of the suture needle and suture material, and the concomitant difficulty in manipulating the reduced-size suture needle through the tissue and the tying of a knot in the suture material, all of which is performed by the surgeon while viewing the surgical site through various image magnifying devices. With respect to endoscopic surgery, suturing and tying knots represent an even more time consuming procedure due to the narrow confines of the endoscopic instruments. Accordingly, while endoscopic surgery would be preferred for many surgical procedures, the advantages are often outweighed by the disadvantages caused by the length of time required to complete the endoscopic surgical procedure, which time is greatly extended due to the difficulty and amount of time required for suturing.

There have been many attempts to provide devices to take the place of conventional suturing with a suture needle and a length of suture material. However, such prior art devices have essentially consisted of staples, clips, clamps, or other fasteners that do not provide the adjustability in tension that can be obtained by the surgeon incident knotting and advancing a length of suture material to the tissue to be sutured. U.S. Pat. Nos. 3,827,277 to Weston; 4,060,089 to Noiles; 4,490,326 to Beroff et al.; 4,513,746 to Aranyi et al.; 4,532,926 to O' Holla; 4,548,202 to Duncan; 4,573,469 to Golden; 4,590,937 to Deniega; 4,595,007 to Meride; 4,602,634 to Barkley; 4,646,741 to Smith; 4,671,280 to Dorband et al.; 4,719,917 to Barrows et al; and 4,741,337 to Smith et al. are representative of such prior art devices for use in place of conventional suturing. Many of these prior art devices are made of bioabsorbable materials such that the devices are absorbed over time into the bodily tissue and do not have to be removed after the tissue has healed.

There exist many compositions useful as bioabsorbable materials, as represented by the above patents and by U.S. Pat. Nos. 3,739,773 to Schmitt et al.; 3,797,499 to Schneider; 4,141,087 to Shalaby et al.; 4,300,565 and 4,523,591 to Kaplan et al.; and 4,649,921 to Koelmel et al., which discuss characteristics of various bioabsorbable materials and medical devices desirably manufactured of such materials, such medical devices being of a type designed to be engaged in, embedded in, or otherwise attached to various types of bodily tissue, such as bone, muscle, internal organs, skin and other soft tissue, to remain in place in the tissue until the device is absorbed into the body.

U.S. Pat. Nos. 3,570,497 to Lemole discloses a suture device formed of a needle with a piercing point extending from a latch cord carrying notches designed to pass through a latch collar. The latch cord is resilient so as to be curved upon itself to form a suture stitch without requiring tying of knot. However, the latching function does not provide the same degree of tension control as can be obtained from knotting a length of suture material. U.S. Pat. No. 4,548,202 to Duncan discloses use of a similar structure in a tissue fastener device, in that serrations or angled barbs are provided along spaced legs passing through tissue to be engaged by an apertured receiver or a flexible filament mesh. U.S. Pat. No. 3,123,077 to Alcamo discloses a surgical suture device having raised projections, depressions or teeth such as barbs or spicules to snag or penetrate tissue so as to hold a sewn incision or wound.

Surgical clips and staples have also been proposed as substitutes for conventional suturing practices. Such clips and staples are used principally to ligate tubular bodies such as blood vessels during open surgical procedures, as well as for skin closure devices. However, these known structures have proven to be not entirely reliable ligating and tissue approximation devices, as the ends of the respective devices tend to separate over time, particularly when used in areas such as fluid vessels and skin folds where they are subjected to variations in pressure and/or tension.

Endoscopic surgery is generally preferred over open surgery due to the greatly reduced trauma and wound healing time for the patient, and due to the concomitant cost savings associated with shorter hospital stays and the ability to perform some forths of surgery without general anesthesia and in non-hospital or outpatient surgery sites. Accordingly, there has been much effort spent to develop techniques to facilitate suturing so as to further reduce the total duration of surgical procedures. Alternative suturing techniques that have been proposed have included electric coagulation, mechanical devices such as clips, clamps and staples, and lasers. However, no well-accepted alternative has yet been found, since suturing and tying are essential and vital parts of most surgical procedures due to the advantages discussed above with respect to the known alternatives. That is, to date, the proposed alternatives have had disadvantages which outweigh any benefits they may have conferred, chief amongst the disadvantages being an increased health and safety risk to the patient. Furthermore, these proposed suturing devices and procedures do not provide the surgeon with the advantages of suturing and tying and, as a whole, are not useful in a wide range of procedures to allow expansion of the areas in which endoscopic surgery can be effectively performed. Thus, there is a great need for new and advanced suture devices, particularly ones that are applicable in endoscopic surgery, that afford surgeons all of the advantages of knot tying and suture tensioning, and which can be applied in a time-efficient and effective manner.

SUMMARY OF THE INVENTION

Accordingly, it is an object of the present invention to provide a variety of suture tie devices and clips that are particularly useful in endoscopic surgery and that overcome the above-mentioned disadvantages of the prior art suture tie devices.

Another object of the present invention is to eliminate conventional, time consuming suturing and tying procedures associated with many surgical procedures by providing a variety of suture tie devices clips and applicators therefor that permit surgical procedures such as vessel ligation, wound closure, suturing and tying functions to be accomplished simply and expediently.

A further object of the present invention is to replace conventional suture needles and clips with suture tie devices and adjustably tensionable clips capable of penetrating tissue and forming a suture loop of user-selectable and variable size to provide the surgeon with a high degree of suture tying control.

Another object of the present invention is to provide a variety of applicators for manipulating and applying various configurations of suture tie devices.

The present invention relates generally to suture tie devices surgical clips for suturing bodily tissue that is formed of one or more legs of suture material. A locking/tying member can optionally be provided that is selectively displaceable along one or more of the device legs so as to cooperate with the distal portion of the device to form a suture loop. The one or more legs can be configured as a tissue penetrating or grasping leg to further facilitate installation of the suture tie device. In alternate arrangements, the suture tie device can be formed from a predetermined length of flexible or semi-rigid bio-absorbable or non-bioabsorbable material. The locking/tying member can be arranged to be selectively displaceable along the length of suture material and can be dimensioned to receive a free end of the suture material so as to form a suture loop. The locking member can also be configured as a rigid, semi-rigid or generally elastic member and can be arranged so as to be displaceable along the device leg or length of suture material in a predetermined single direction only, or to be bi-directionally displaceable therealong.

An applicator for suturing bodily tissue with one or more suture tie devices such as those described above is also provided. The applicator includes means for storing a plurality of suture tie devices, and actuating means for delivering a suture tie device from the storing means to one or more distal penetrating needles or forceps such that a plurality of sutures can be placed in the bodily tissue without removing the applicator from the suture site. Means is provided for penetrating the tissue to be sutured and for engaging and/or displacing the locking/tying member of the suture tie device relative to the device leg or suture material to effect suture tying.

The invention relates further to methods of suturing bodily tissue, occluding tubular vessels, and closing tissue apertures. The suturing method includes the steps of penetrating the bodily tissue with the distal end of one or more applicator needles, forceps, or the leg of the suture tie device, and selectively displacing a locking/tying member along the tissue penetrating leg or length of suture material toward the distal end thereof to a position at which the locking/tying member cooperates with the distal end to form a suture loop. The suture loop can be appropriately tensioned to provide the desired extent of tissue approximation.

BRIEF DESCRIPTION OF THE DRAWINGS

Further objects and advantages of the present invention will become apparent from the following description of the preferred embodiments taken in conjunction with the accompanying drawings, in which:

FIG. 1 is a sectional side view of a suture tie device in accordance with the present invention;

FIGS. 2 and 3 are sectional side views of the suture tie device of FIG. 1 during and after suturing, respectively;

FIGS. 4, 5, 6, 7, 8, and 10 are sectional side views of alternative aspects of the suture tie device depicted in FIG. 1;

FIG. 9 is a cross-sectional view of the suture tie device depicted in FIG. 8 with a portion thereof removed to illustrate further details of the device;

FIGS. 11, 12, 13 and 14 are sectional side views of alternative aspects of the suture tie device according to the present invention in which the locking/tying members thereof are arranged so as to be selectively displaceable in either the distal or proximal direction;

FIG. 15 is an exploded sectional side view of a further alternative aspect of a suture tie device according to the present invention;

FIG. 16 is a sectional side view of an alternative configuration of a tissue penetrating leg for use in the device depicted in FIG. 15;

FIGS. 17 and 18 are sectional side views of a further aspect of a suture tie device according to the present invention;

FIGS. 19A through 19C are sectional side views of an alternative arrangement of a suture tie device according to the present invention illustrating various stages of engagement incident to suturing;

FIG. 20 is an exploded side view of a modification of the suture tie device depicted in FIGS. 19A through 19C;

FIG. 21 is a side view, partly in section, of one embodiment of an applicator for the application of suture tie devices illustrated in FIGS. 1 through 20 of the present invention;

FIG. 22A is a side view of the distal portion of the outer tubular member of the applicator of FIG. 21;

FIG. 22B is a frontal view of the inner cartridge tubular member of the applicator of FIG. 21;

FIG. 22C is a side view, partially in section, of an inner cartridge tubular member of the applicator of FIG. 21 showing further details of its structure;

FIGS. 22D and 22E are sectional side views of modifications of the extendable actuating rod of the device depicted in FIG. 21D;

FIG. 23 is a side view, partially in section, of an alternative arrangement of a suture tie device applicator;

FIG. 24A is a side view of the distal portion the outer tubular member of the applicator of FIG. 23;

FIG. 24B is a frontal view of the inner cartridge tubular member of the applicator of FIG. 23 showing the arrangement of guide members for advancing the locking/tying member of each suture tie device;

FIG. 24C is a sectional side view of the distal portion of the inner cartridge tubular member of the applicator of FIG. 23:

FIG. 25 is a side view, partially in section, of a further arrangement for a suture tie device applicator according to the present invention for the application of suture tie devices illustrated in FIGS. 1 through 20;

FIG. 26 is a sectional side view of the cartridge and intermediate tubular members of the applicator of FIG. 25;

FIG. 27 is a side view, partially in section, of a further arrangement for a suture tie device applicator according to the present invention;

FIG. 28 is a sectional side view of the distal portion of the applicator of FIG. 27;

FIG. 29 is a side view, partially in section, of a further embodiment of a suture tie device applicator according to the present invention;

FIG. 30 is a sectional side view of a further arrangement for a suture tie device according to the present invention;

FIGS. 31 and 35 are sectional side views of various arrangements for the distal portions of the inner cartridge and intermediate tubular members of various embodiments of the suture tie device applicators of FIGS. 21, 23, 25, 27, 29 and 37;

FIGS. 32-34 are frontal views of various arrangements for the distal end of the curved portions of either the intermediate and/or cartridge tubular member of the applicators of FIGS. 25, 27, 29 and 30, respectively;

FIGS. 36A and 37 through 42 are sectional side views illustrating various configurations of a multiple-leg suture tie device in accordance with the subject invention;

FIG. 36B depicts a sectional side view of the locking/tying member of FIG. 36A;

FIGS. 44A and 44B are side views, partially in section, of various configurations for the distal ends of the suture tie devices depicted in FIGS. 40 and 41;

FIGS. 45A–45D are broken side views, partially in section, of various configurations for the distal ends of the suture tie device depicted in FIGS. 40 and 41;

FIGS. 46 and 47 are broken isometric views depicting sections of the leg portions of the suture tie devices of the subject invention;

FIGS. 48A and 48B illustrate use of the device depicted in FIG. 36A in closing off tubular member;

FIGS. 49A–49C illustrate in sequence use of the device depicted in FIG. 37 during suturing;

FIG. 50 is a broken section showing the use of the suture tie device of FIG. 37 foreclosing a tissue aperture;

FIG. 52 is a sectional side view of an applicator for applying the multiple leg suture tie devices of the subject invention;

FIG. 53 is an enlarged view of a portion of the applicator of FIG. 52;

FIGS. 54 and 59 are side view of the distal end of the applicator depicted in FIG. 52 at different stages of operation;

FIG. 55 is an end view of the applicator segment depicted in FIG. 54;

FIGS. 56 and 57 are side views of alternative arrangements for the distal end of the device of FIGS. 52 and 53;

FIG. 58 is a sectional side view showing further details of the distal end of the applicator depicted in FIGS. 52 an 53;

FIG. 60 is a side view of an alternative distal end adjusting mechanism for use with the applicator depicted in FIGS. 52 and 53;

FIGS. 68A and 68B are side and end views, respectively, of the distal end of one of the applicator tubular members;

FIG. 69 is a sectional side view of the distal end of the applicator and forceps thereof of FIG. 61 with a suture tie device mounted therein;

FIG. 70 is a perspective side view of an alternative embodiment of a surgical clip;

FIG. 71 is a perspetive side view of a further alternative embodiment of a surgical clip; and FIG. 72 is a perspective side view of an alternative embodiment of the structure depicted in FIG. 71.

DETAILED DESCRIPTION OF THE PREFERRED EMBODIMENTS

Figures 43A, 43B, 43C:
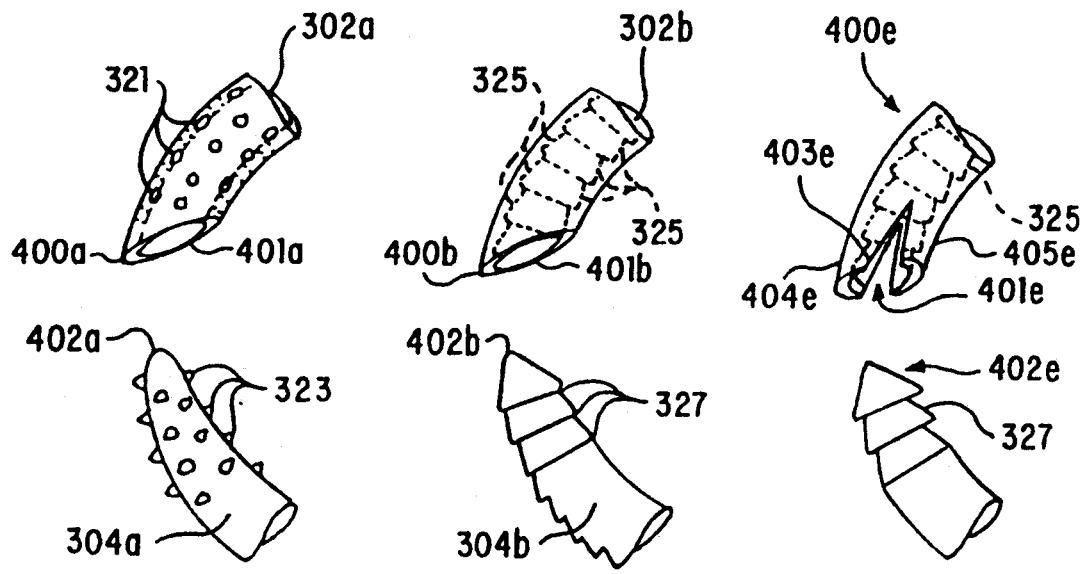
FIGS. 43A–43F are side views, partially in section, of various configurations for the distal ends of the suture tie devices depicted in FIGS. 36A–39.

With reference to the drawings, wherein like reference characters correspond to like components throughout the various views, and with particular reference to FIGS. 1 through 3, there is depicted a suture tie device 30 in accordance with the present invention that includes a leg 32 having a preferably rigid proximal portion 34 of relatively large diameter and a distal tissue penetrating portion 36 of diminished diameter. As used throughout this disclosure, the term "proximal" and variants thereof refers to the right hand side of a drawing, whereas the term "distal" and its variants refer to the left hand side of the drawing. The distal portion 36 is provided with a suture needle or hook-like or curved configuration that terminates at a sharp distal end 38 and defines a tissue receiving space 39 having an open side adjacent distal end 38 that is positioned between the distal end 38 and the leg 32. The curved configuration of the distal tissue penetrating portion 36 is similar to the configuration of a conventional suture needle and, preferably, is slender and configured so as to taper inwardly to a sharp point at its distal end 38. A locking/tying member 40 at least partially, and preferably substantially, circumscribes the proximal portion 34 of the device 30 in a ring-like fashion. Any one or both of the leg 32 and locking/tying member 40 can be completely or partially formed of a bioabsorbable or non-bioabsorbable material, or a combination thereof, which can be provided with appropriate physical characteristics so as to be entirely or partially rigid, semi-rigid or flexible, elastic, resilient or malleable in accordance with the suture tie device's 30 intended utilization. The locking/tying member 40 is preferably formed as a rigid or semi-rigid member and defines a passage 41 extending therethrough having an internal configuration or luminal surface that is configured to cooperate with a plurality of angled teeth 42 protruding from the outer surface of the leg 32 such that the locking/tying member 40 is selectively displaceable only distally, in the direction of arrow A (FIG. 1), from the proximal end toward the distal end of leg 32.

As illustrated in FIG. 2, the interior surface of the locking/tying men, her 40 is preferably provided with a plurality of angled teeth 44 arranged at complementary angles to the angle of the teeth 42 of the leg 32 for engaging the leg teeth 42 to prevent proximal, i.e., rearward, movement of the locking/tying member 40. The angled teeth 42 can be disposed along the leg 32 in a variety of configurations, such as to extend from the entire or a predetermined portion of the peripheral surface of the leg, or so as to extend from a longitudinal recess or groove formed along the length of the leg 32. Furthermore, various configurations can be utilized to permit only the distal movement of the locking/tying member 40. Such movement-restricting configurations include whisker-like filaments, barbs, ridges, angled pins or other protrusions which extend from the leg, some or all of which can be angled in the distal direction to prevent the proximal movement of a locking/tying member 40.

In use, the suture tie device 30 is held in a cradle of an applicator, examples of which are seen in FIGS. 21, 23, 25, 27 and 29 and described in detail below, and manipulated in a manner similar to the movement of a conventional suture needle so as to extend the sharp distal end 38 of the device to penetrate tissue to be sutured, with or without the assistance in tissue penetration of the various suture tie device applicators described below. Once the tissue penetrating portion 36 has been manipulated so as to extend through the tissue, the locking/tying member 40 is displaced distally toward the distal end 38, as illustrated in FIG. 2, to cooperate with the distal tissue penetrating portion 36 to close or substantially close the open side of the tissue receiving space 39 and form a suture loop with the tissue engaged thereby. The extent of distal movement of the locking/tying member 40 determines the size of the suture loop, the compression on the tissue sutured thereby, and ultimately completion of the tying of the suture loop. The degree of tension of the tie can also be adjustable by the movement of the locking/tying member distally from a position of initial approximation of the tissue structures to a position of full tying of the suture loop with maximum tension of the tie. Once the locking/tying member 40 has been moved the desired extent to securely tie the suture loop to a desired degree of tension, the protruding proximal portion of the leg extending beyond the locking/tying member 40 can be severed, as shown by severing line "S" in FIG. 2, at an appropriate position to allow the tied suture loop to remain intact. The severed portion of the leg can thereafter be removed from the surgical site for disposal.

A modified suture tie device 48 according to the present invention is illustrated in FIG. 4. The modified device 48 differs from suture tie device 30 depicted in FIGS. 1–3 primarily in the configuration of the leg and locking/tying member. To this end, the distal portion 50 of leg 52 has more of a curved suture needle-like or hook-like configuration for grasping a larger amount of tissue, whereas the proximal portion 54 thereof is of comparatively smaller diameter. The locking/tying member 56 is provided with a central passage 58 therethrough having a plurality of angled teeth protruding therefrom to engage correspondingly-angled teeth 60 protruding from the leg. As mentioned above, these teeth-like coupling configurations can be replaced with other types of protrusions or indentations which also inhibit or prevent undesired proximal movement of the locking/tying member. A small recess 62 can be provided at the upper, distal end of locking/tying member 56 to receive the sharp distal end 64 of the tissue penetrating distal portion 50, while a larger recess 66 having a plurality of angled teeth or other suitable leg protrusion-engaging members 44 therealong to cooperate with and receive the angled teeth or other protruding members 60 along the curved distal portion can be provided at the lower of the locking/tying member. Accordingly, the sharp distal point 64 of the suture tie device can be protected from exposure to surrounding structures, surgical instruments and the like by being received in recess 62, while recess 66 accommodates the curvature of the distal portion of the suture tie device to allow the movement of the locking/tying member 56 therealong as desired to produce the desired degree of locking tension for tissue approximation and/or suture tying.

The suture tie device 68 illustrated in FIG. 5 is substantially similar to the embodiments described above and depicted in FIGS. 1–4, with the exception that the proximal portion 70 of the tissue penetrating leg 72 is configured so as to extend through a passage 74 formed in the bottom of locking/tying member 76. The locking/tying member is provided with a protruding portion 78 which extends outwardly from its distal face. The distal end of the protruding portion 78 includes a recessed space 77 that is dimensioned to accommodate the curved distal portion 71 of the penetrating leg 72 and any tissue sutured thereby. A recess 80 is formed in the member 76 to receive the sharp distal end 82 of the tissue penetrating distal portion 71 upon engagement of the distal portion with the locking/tying member. The tissue receiving space 79 is configured so as to be generally more open, i.e., less restricted by leg 70, than corresponding space 39 of the arrangement described in FIGS. 1-4; however, the lateral, open sides of tissue receiving space 79 are likewise arranged so as to be selectively closable by the locking/tying member 76 to tie the suture loop.

The suture tie device 84 illustrated in FIG. 6 depicts a further modification of the suture tie device of the subject application as depicted in FIG. 5, with the exception that the tissue penetrating leg 86 has a distal portion which can be provided with either a triangular 85 or rectangular 85' (depicted in phantom) cross-sectional configuration. The triangular configuration 85 is preferred, for it provides for the secure grasping and suturing of a relatively greater amount of tissue. The distal face of the locking/tying member 84 can be provided with a variety of different configurations, such as with a generally planar face, as shown at 83', and optionally as with a recessed space 77 to accommodate the tissue sutured by distal portion 85'. Alternatively, the distal face can be configured to provide a generally triangular or pyramidal protrusion 83 (depicted in phantom) that can optionally be provided with a recessed space 77 at the distal tip of protrusion 83 to accommodate the tissue sutured by angularly-configured distal portion 85.

The suture tie device 88, illustrated in FIG. 7, is similar to the suture tie device 48 depicted in FIG. 4 and described above, with the exception that the proximal portion 90 of the leg 32 passes through a passage 41 formed at the top of locking/tying member 92 to create a relatively large, generally "C" or "V"-shaped space 91 in the curved suture needle-like, tissue-penetrating distal portion 94. By providing a slight proximally-extending, needle-like protrusion 93 extending from tissue-penetrating portion 94, a plurality of segments of tissue can be engaged within spaces 91 and 95 thereof and simultaneously tied by the distal movement of locking/tying member 92 along leg 32 in the manner described above.

The arrangement of the suture tie device 96 shown in FIGS. 8 and 9 provides a relatively elongated, narrow, hook-like tissue penetrating distal portion 98 with a relatively thick proximal leg portion 100. A longitudinal groove 101 is disposed along the upper and lower length of the leg thereof within which are provided a plurality of slight ridges 102 and recesses 103 that are adapted to cooperate with the plurality of angled filaments 104 extending from the internal surface of the central passage of the locking/tying member 106 so as to provide selectively actuable groove coupling means. The filaments are angled such that the locking/tying member can be selectively displaced in a distal direction only. The locking/tying member and groove coupling means described above and illustrated in FIGS. 8 and 9 can be reversed such that the filaments 104 extend from leg 100 of the suture tie device and cooperate with ridges 102 or recesses 103 along the internal surface of the locking/tying member's central passage. Suture tie device 96 is particularly useful for plugging or occluding holes in tissue or organ structures and for suturing damaged regions which are located in deep and/or narrow spaces, since the shape of the spaces defined by the distal tissue penetrating portion 98 is relatively narrow and ovate.

As seen in FIG. 10, suture tie device 96' can also be provided with a plurality of whisker-like filaments 105 on the surface of the leg 100 that are angled to cooperate with indentations, grooves, or micro-holes 104' formed along the interior of the passage of the locking/tying member 106' to ensure unidirectional, distal movement of the locking/tying member while preventing its proximal (backward) movement.

FIG. 11 shows a suture tie device modification 97 of the suture tie device 96 depicted in FIGS. 8 and 9 that provides for bi-directional movement of the locking member along the leg of the device. In the depicted arrangement of FIG. 10, the leg 100 of the device is configured as a generally hollow tubular member and is provided along its inner surface with a plurality of tooth-like protrusions 109. Mounted within the central passage 41 of the locking/tying member 107 is a pair of opposed, inwardly-protruding arms 111 which pass through longitudinal slots 113 formed along the upper and lower sides of the tissue penetrating leg 100. Attached to the ends of each arm 111 is a plate 115 having a plurality of tooth-like protrusions 117 on the sides which face the protruding teeth 109 of the leg. In this leg engaging arrangement, the locking/tying member 107 is configured as an elastically-deformable member, and a predetermined amount of space is provided between the passage wall of the locking/tying member and the outer surface of the penetrating leg 100 such that, when the locking/tying member 107 is compressed along its upper and lower surfaces, the plate's teeth 117 disengage from the leg's inner teeth 109 to disengage the locking/tying member from the leg to permit selective distal or proximal movement along the leg. However, once the locking/tying member 107 is released, the plate's teeth 117 engage with the leg's internal teeth 109 such that the locking/tying member is locked at that position.

FIG. 12 shows a modification 177 of the components for the bi-directionally operable locking/tying member and leg-engaging means described in FIG. 11, in which the hollow leg 100 of the suture tie device is provided with a plurality of microholes 123 along its interior surface. The locking/tying member 125 is provided with a pair of opposed arms 119 which protrude inwardly and pass through longitudinal slots 127 along the upper and lower sides of the leg of the suture tie device. Positioned at the free end of each arm is one or more hook-like members 121 which cooperate with the microholes 123 of the leg to lock the locking/tying member 125 in place on the leg. When the locking/tying member is compressed as described above, the member 125 can be selectively displaced distally or proximally along the leg 100 to a desired position, where it can then be locked into position upon release of the locking/tying member, thereby urging the hook-like members 121 to extend into the microholes 123 in the manner described above with the plate teeth 117 and leg internal teeth 109.

FIG. 13 shows suture tie device 129 in which the bi-directionally operable locking/tying member 131 is provided with a pair of recesses 133 and 135 to accommodate distal penetrating portion 137 and sharp distal tip 139, respectively, when the locking/tying member 131 is moved distally. Positioned on the surface of the leg are a plurality of umbilicated grooves or ridges 145 which can cooperate with the ends of inwardly-extending pivoting bars 143 of the locking/tying member 131. These pivoting bars 143 extend outwardly from recess 41 to a pivoting point 141, which joins each pivoting bar 143 to a corresponding rigid bar 119' which extends from the interior surface of the device 131 into its internal passage 41. The pivoting bar 143 is angled to an end which can cooperate with the grooves 145. When the locking/tying member 13 is compressed from the top and bottom, bars 119' move inwardly, causing the angled bars 143 to collapse away from the leg by the pivot point to permit movement of the locking/tying member in either direction, distally or proximally, until it reaches a desired position, at which point the locking/tying member can be released and the pivoting bars 143 returned to their initial position with their ends locked within the grooves of the leg to lock the locking/tying member in place along the leg.

FIG. 14 illustrates a modification 147 of suture tie devices 97 and 177, in which the bi-directionally operable locking/tying member 149 is provided with a pair of opposed bilateral bars or rods 151 which protrude inwardly from plates 151'. Each bar or rod 151 is provided with a longitudinally oriented plate or bar 153 having a plurality of hook-like members 155 which can cooperate with the microholes 123 formed in the leg of the device 147. The hollow leg of suture tie device 147 is provided with a pair of bilateral slots 127 extending longitudinally to allow bilateral bars 151 of the locking/tying member to move distally and proximally upon compression and advancement of the locking/tying member. Microholes 123 accommodate the hook-like members 155 when the locking/tying member is released to lock the device 149 at a desired position along the surface of the leg 100. All of the locking/tying members illustrated in FIGS. 11-14 are preferably made of a rigid or semi-rigid resilient or elastic bioabsorbable or non-bioabsorbable material to facilitate control of its distal and proximal movement.

A further suture tie device arrangement is depicted at 108 in FIG. 15 and includes a tissue penetrating leg 110 having a polygonally-shaped distal tissue penetrating portion 112 which terminates at a sharp distal end 114 and a proximal shoulder 25, as shown in FIG. 15, or a tissue penetrating leg 110' having a generally rectangular distal tissue penetrating end 112' terminating at a sharp distal point 114 and proximal shoulder 25, as shown in FIG. 16. A locking/tying member 116 is provided with a passage 118 that extends through the bottom thereof for either leg 110 or 110', and a recess 120 at the top for receiving distal end 114 when the locking/tying member 116 is moved distally to tie the suture loop. When the locking/tying member 116 is utilized alone with either leg 110 or 110', the locking/tying member itself can be moved distally to tie the suture loop.

An alternative to using locking/tying member 116 alone is to use a combination of locking/tying member 116 in connection with a plug 122 with either leg 110 or 110'. The polygonally shaped distal end 126 of the plug 122 corresponds to the polygonally-shaped distal portion 112 of leg 110, whereas the blunt distal end 126' (depicted in phantom) corresponds to the rectangular distal portion 112' for use therewith. When the plug 122 is used with the leg 110, the proximal portion of leg 110' passes through the lower passage 118 of locking/tying member 116, which is provided with a relatively wide central passage 119 for receiving plug 122. A plurality of barbs 124, ridges, filaments, or microholes can be formed on the surface of plug 122 to correspond to protrusions along the internal surface of passage 119 to permit for selective displacement of the plug 122 only in the distal direction until its proximal shoulder 123 meets the proximal face of locking/tying member 116, thereby tying the adjustable suture loop. Alternatively, because the use of both the plug 122 and the locking/tying member 116 provides both a proximal movement of leg 110 or 110' and a simultaneous distal movement of plug 122 in relation to locking/tying member 116, the cavities 118 and 119, as well as the leg and plug members 110, 122 can be appropriately dimensioned such that simultaneous movement of the leg 110 and plug 122 toward each other allows the tightening of the plug and the leg, even in the absence of any coupling means on the surfaces of either the plug or the leg.

A further arrangement for a suture tie device 128, illustrated in FIG. 17, includes a tubular or hollow tissue penetrating leg 130 which defines a cavity 131 and includes a distal tissue penetrating portion 132 terminating at an open sharp distal end 134 and an outwardly flared or tapered proximal shoulder 135. The locking/tying member 136 is provided with upper and lower passages 138 and 140, respectively, for receiving rigid or semi-flexible upper and lower arms 142 and 144 which extend in a distal direction from a push plate 146. The proximal shoulder 135 of the leg 130 extends through the lower passage 140 of locking/tying member 136 to prevent the leg 130 from passing distally outwardly therethrough. The arms 142 and 144 have a diameter selected to permit them to be received within the respective passages 138 and 140 such that the distal end 134 of the leg 130 can be received into the distal end of arm 142' instead of receiving the distal end of arm 142 internally. In operation, after tissue penetration, the push plate 146 is moved distally such that the distal portion of arm 142 or 142' enters or receives the distal end 134 of the leg 130, and the lower arm 144 passes through the lumen of leg 130 until plate 146 meets the proximal shoulder of leg 130, thereby completing a suture loop which can, thereafter, be adjusted in size by the movement of locking/tying member 136 distally until the loop is ultimately tied and tensioned. As described above, one-way movement of the locking/tying member 136 can be effected by suitable coupling means as described above.

A suture tie device 148 as illustrated in FIG. 18 depicts another arrangement for creating a suture loop by providing for a length of suture material to circulate through the leg of the suture tie device instead of having the locking/tying member contact with the distal end of the leg to create the suture loop. The suture tie device 148 includes a hollow tissue penetrating leg 150 having a proximal shoulder 135, and a locking/tying member 152, all of which are similar to the like components described above in connection with FIG. 17. The suture tie device 148 further includes a length of suture material 154 which can be rigid, semi-rigid, flexible, malleable or resilient, bioabsorbable, or non-bioabsorbable, that is provided with a small, outwardly-extending or tapered proximal shoulder 155 which is dimensioned so as to inhibit passage through the upper passage of locking/tying member 152. This length of suture material passes distally through the upper passage 138 of the locking/tying member 152 to be received internally in the open distal end 156 of the tissue penetrating distal portion of leg 150 to complete a suture loop. Once the suture material has been received in the leg 150, the locking/tying member 152 can be moved in a one-way fashion distally to diminish the size of the suture loop until it is completely tied. Alternatively, a length of suture material 154' can be provided that is entirely or partially hollow, and leg 150 can be configured so as to be either hollow or solid, such that the hollow suture material 154', when pushed distally through the upper passage of locking/tying member 152, receives the sharp open or closed distal end 156 internally rather than passing into the leg to create a suture loop. Thereafter, locking/tying member 152 can be moved distally to diminish the size of the suture loop until it is completely tied. As a further alternative, a length of solid suture material 154 can be passed distally through the proximal end of hollow leg 150 located within the lower passage 140 of locking/tying member 152 until the suture material 154 passes distally through the entire leg 150 and exits proximally out of the open distal end 156. The suture material 154 can then passed proximally through the upper passage of locking/tying member 152 to complete the suture loop. Thereafter, locking/tying member 152 can be moved in a one-way (unidirectional) fashion distally to diminish the size of the suture loop until the loop is appropriately tied and tensioned.

A further configuration of a suture tie device 158 is illustrated in FIGS. 19A, 19B and 19C and includes a solid tissue penetrating leg 160 having a proximal ring 162 extending therefrom and a distal tissue penetrating portion 164 terminating at a sharp distal end 38'. A locking/tying member 166 is provided in the form of a plug which may have coupling members 168 such as angled teeth, ridges, or filaments extending therefrom for cooperating with a correspondingly-configured internal surface of a leg collar 162. A nib 170 can be provided which extends from the upper end of the plug-like locking/tying member 166 to overlie the sharp distal end 38' of the tissue penetrating portion 164. In use, the plug operates in a fashion similar to the ring-like locking/tying members described above by passing through the collar 162, as illustrated in FIGS. 19B and 19C, in a distal direction to a desired extent to capture tissue sutured by the tissue penetrating distal portion 164. A gently curved recess 165 can optionally be formed along the curved convex distal end of locking/tying member 166 to accommodate the sutured tissue or the curved distal portion 164 of leg 160 alone when plug 166 is moved distally through collar 162, as shown in FIGS. 19B and 19C. In FIG. 19C, the sharp distal end 38' is depicted as being completely covered by nib 170, and the curved distal portion 164 of leg 160 is received by the recess 165, as would occur upon complete distal advancement of the locking/tying member 166 relative to the collar 162.

FIG. 20 shows a modification 158' of the suture tie device 158 shown in FIG. 19A, in which the cradle-like penetrating leg 160' is provided with a generally U-shaped or C-shaped cross-section to create a channel or space 161 for accommodating the suture tissue and/or to allow the passage of a length of suture material therethrough. The channel 161 which is continuous with the central passage of the collar 162' located at the proximal end of leg 160'. The plug-like locking/tying member 166' can be provided with a coupling configuration similar to that described in FIG. 19A. In addition, plug 166' can also be provided with a lumen or channel 167 which extends along the lower side, the distal curved end, and the upper side to provide for the passage of a length of suture material or medication therethrough.

As will be appreciated from the above discussion of various embodiments of suture tie devices according to the present invention, the curved suture needle-like or hook-like tissue penetrating distal portions can be provided with a wide variety of configurations to define spaces therein of various shapes and configurations, such as circular, oval, rectangular, rhomboid and the like, for suturing various tissue and organ structures. The locking/tying members can be arranged so as to be movable only distally along the tissue penetrating legs in a single direction only by means of various cooperating structures such as continuous or segmented barbs, angled teeth, whisker-like filaments, microholes for engagement by corresponding microfilaments and the like, or-this one-way movement may be achieved by the use of umbilicated, thread-like ridges embedded in a groove extending along the length of the leg so as to engage and lock whisker-like filaments or angled pins or the like protruding from the internal surface of the locking/tying member. The locking/tying members can also be arranged so as to be bi-directionally displaceable along the legs either direction by having either through the provision of hollow penetrating legs with teeth or microholes or the like and longitudinal slots which allow for distal and proximal movement of the protruding arms of the locking/tying members. The locking/tying members can bs provided with plates with teeth or hooks which correspond to the internal surface configurations of the legs, or with solid penetrating legs having grooves on the surface which cooperate with pivoting bars or rods extending from the internal passage of the locking/tying members. Compression of these various locking/tying members allows their distal or proximal movement, while their release locks the locking/tying member in the desired position. The locking/tying members themselves can also be provided with a wide variety of shapes and cross-sectional configurations. Similarly, in accordance with the configuration of the distal tissue penetrating portions, complementary recesses can be formed in the locking/tying member to accommodate and cover the distal portion including the sharp distal end, and further to accommodate tissue penetrated by the distal end such that the tissue is held within the suture loop formed by the locking/tying member and the tissue penetrating leg. The suturing procedure is essentially the same with all of the embodiments in that a suturing maneuver is made with the distal end of the suture tie device alone or in conjunction with the distal end of an applicator as described below to penetrate the tissue, and a looping and tying operation is provided by moving the locking/tying member distally a desired extent until the suture loop is completely tied around the sutured tissue. In accordance with the tissue or organ structure to be sutured, the configuration of the locking/tying member (for example, a ring-like or plug-like member) can be provided with a distal face having a configuration to accommodate the tissue as well as the sharp edges of the distal portion of the tissue penetrating leg. The sharp distal end can be disposed within the locking/tying member in accordance with the tissue or organ structure to be sutured and its position in the body. While the suture tie devices described above are preferably and advantageously made of bioabsorbable material, the suture tie devices can be made in whole or in part of partially bioabsorbable or non-bioabsorbable material, if desired. In addition, the locking/tying members can be configured so as to be rigid or resilient depending on the arrangement of the locking, tying, and/or coupling means.

With reference to FIG. 21, there is depicted an applicator 172 comprised generally of two tubular members: a cartridge member 174 and an outer tubular member 206 having a tubular lumen for receiving the cartridge member. The applicator 172 allows for the application of the various suture tie devices described above and depicted in FIGS. 1–20 in accordance with the present invention. FIG. 22A shows the distal portion of only the outer tubular member 206 with its hook-like cradle 208 for receiving one of the suture tie devices 48 for application to tissue in the manner described in detail below. The cartridge 174, which is shown in further detail in FIGS. 22B and 22C, is a spring-loaded member which houses a plurality of suture tie devices, such as the suture tie device 48 shown in FIG. 4, in an end-to-end serial arrangement.

With reference to FIG. 21, the cartridge 174 includes an outer tubular member 176 having a cap 178 at is proximal end with an extendable rod 180 passing through an opening in cap 178 and terminating at its proximal end at an actuator button 182 and at its distal end at a pusher member 184 having a recess therein adapted to receive the proximal end of the last (i.e., most proximally positioned) of the plurality of suture tie devices 48. Various means can be provided for the extending mechanism of the rod 180, some of which are shown in FIGS. 22C, 22D and 22E. The rod 180 can be configured as two or more concentrically-arranged tubular members 180a, 180b which have cooperating configurations for extending the length of the rod and locking it at a selected length such that a single suture tie device can be released in a one-by-one fashion. For example, one of the outer or inner concentrically-arranged rode 180a, 180b can be provided with a plurality of one-way angled filaments or pins 181, and the other of the tubular members can be provided with corresponding umbilicated threaded grooves or ridges 183, as shown in FIGS. 22C and 22D. Alternatively, the rods 180a and 180b can be provided with correspondingly-threaded surfaces 185, as shown in FIG. 22E, to ensure displacement in the desired direction.

A helical spring 186, depicted in FIG. 21, is mounted in a displaceable housing 187 in compression between actuator button 182 and cap 178. Positioned within cartridge tubular member 176 is a biasing means 188 such as helical spring member, which is mounted in compression between the proximal end of the tubular member 176 and pusher member 184. The distal end of the cartridge 176 is slotted to define two or more expandable arms 190 and 192, as seen frontally in FIG. 22B. The arms terminate at ends 194 and 196, respectively, and are each provided with a generally curved configuration which can be varied in shape to accommodate the curved shape of the distal penetrating portion of the various suture tie devices shown in FIGS. 1–20.

A generally U-shaped or C-shaped handle 198 is provided for controlling operation of the applicator device 172. The handle 198 includes proximal and distal arms 199 and 200 joined to one another by curved spring portion 201. The proximal handle arm 199 terminates at a collar 214 secured to the tubular member 176 that is telescopically received within outer member 206. The distal handle arm 200 terminates at a collar 204 that is secured to the proximal end of the outer tubular member 206 of the applicator 172 that, in turn, is attached at the bottom of its distal end to the fixed, hook-like cradle 208. The cradle 208 is provided with a curved distal portion which terminates at distal end 210 that can be configured in a variety of shapes so as to correspond to the configuration of the distal portion of the leg of the particular arrangement of suture tie device to be used with the applicator. The distal end 210 of the outer tubular member can be configured so as to correspond to the length of the distal end 64 of the suture tie device 48, or it can be provided with a length that is slightly longer than the suture tie device 48 and a configuration which permits it to function as a tissue penetrating member. Preferably, the distal end 210 is provided with a sharp distal edge to facilitate suturing. Alternatively, the distal end 210 can be provided with a length that is slightly shorter than that of the suture tie device 48, so that the distal end 64 of the device 48 functions as the tissue penetrating member.

In use, a cartridge 174 is pre-mounted within applicator 172 or inserted through the open proximal end of the applicator upon removal of the cap 178, and the applicator is inserted through an incision or portal formed in the exterior surface of the body of a patient and advanced to a suturing site. By depressing actuating button 182, extendable rod 180 with pusher member 184 is advanced distally to urge a suture tie device distally so as to expand the cartridge arms 190 and 192 from one another and exit the cartridge to be received in the cradle 208. Once the actuating member 182 is released, the arms 190 and 192 return to their generally closed (rest) position such that a space remains between arm distal ends 194 and 196 that is wide enough to allow the proximal portion of the leg of the suture tie device to pass therethrough, thereby allowing the distal ends 194 and 196 to be in position to push the locking/tying member distally. Once the suture tie device is so positioned, the tissue to be sutured can be penetrated by one or both of the (sharpened) distal ends of the suture tie device and the sharp distal point 210 of cradle 208. Once tissue penetration has been completed, handle arms 199 and 200 are squeezed toward one another a predetermined distance to distally advance the cartridge arm distal ends 194 and 196 against the locking/tying member, thereby advancing the locking/tying member distally. The locking/tying member of the device, such as member 56 of the device 48, can be advanced toward the distal end 64 a desired amount to complete a suture loop and capture the sutured tissue therebetween. Once the locking/tying member is suitably positioned such that the suture loop is tied completely Or the tissue is approximated to a desired extent, the handle can be released and the applicator appropriately manipulated so as to deposit the suture tie device in place. Excess material of the suture tie device extending proximally of the locking/tying member can be severed with a conventional forceps instrument.

An alternative arrangement of a concentrically-arranged multi-tubular applicator 218 for applying suture tie devices according to the present invention is illustrated in FIG. 23. Parts of the applicator 218 that are identical or corresponding to parts of applicator 172 are designated by identical reference numbers and are not described again for the sake of brevity. The extendable rod 180 can be configured as two or more concentrically-arranged tubular members, as described above in connection with FIGS. 22C–22E, and can be moved distally and proximally in relation to one another such that the length of the entire rod extends automatically after each suture tie device is sequentially released from the cartridge. Applicator 218 is substantially similar structurally and functionally to applicator 172 (FIG. 21), with the exception that the tubular member 176 of the cartridge terminates at a blunt, open distal end 220, whereas the outer tubular member 206 terminates at its distal end at a plurality of slotted, multiple curved arms 222. The arms 222 can be configured so as to accommodate the curved distal portion of the various types of suture tie devices described above and depicted in FIGS. 1–20.

Mounted within the tubular member 176 are a plurality of spring-like guides 224 for retaining the suture tie devices within the cartridge against the force of spring 188. The guides 224, which are preferably arranged as opposed, distally-angled pairs extending toward the interior of the cartridge member, are provided with generally concave end surfaces (FIG. 24B) to align the suture tie devices so that the arms can collapse against the internal wall of the cartridge tubular member 176, as indicated by the arrows in FIG. 24C, to allow the suture tie devices to be released from the cartridge in a sequential manner. The distal-most guides 224a (FIG. 24C) extend distally beyond the blunt distal end of cartridge member 176 and serve to push the locking/tying member of the released suture tie device in the distal direction to complete the tying process.

Use of the applicator 218 is similar to that described above with respect to applicator 172, in which a suture tie device can be released into the cradle 208 by compressing button 182 toward cap 178. In an alternative aspect of operation, the (inner) tubular member 176 can be rotated in relation to (outer) tubular member 206, or vice versa, to release a suture tie device into the cradle 208. Another applicator arrangement provides that displacement of handle arms 199 and 200 toward one another upon squeezing of the handle 198 directs the blunt distal end 220 and the distal-most guide 224a of the cartridge to expand the arms 222 of the outer tubular member. Further squeezing of the handle causes the curved distal ends of guides 224a to push the locking/tying member of the suture tie device distally to complete the tying function. Thereafter, an independent forcep assembly, such as a biopsy instrument, can be passed through outer tubular member 206 to sever the portion of the suture tie device protruding proximally of the locking/tying member.

A further arrangement for an applicator 226 is illustrated in FIGS. 25 and 26 and is comprised of three concentrically-arranged tubular members, one of the tubular members being a cartridge member 228 for housing a plurality of suture tie devices of the type described above and depicted in FIGS. 1–20 that are serially arranged and spring biased distally by a compression spring 188 in a manner similar to that described above in connection with the cartridge members for the applicators 172 and 218 depicted in FIGS. 21 and 23. With reference to FIG. 26, the distal portion of the cartridge tubular member 230 is provided with a flat, blunt distal end, whereas the distal portion of intermediate tubular member 236 is depicted as having curved expandable arms 240. Alternatively, the respective distal end configurations can be reversed to provide the inner cartridge tubular with inwardly curved ends and the intermediate tubular member with a flat, blunt end. The cartridge 228, as shown in FIG. 25, includes a tubular member 230 having a cap 232 at its proximal end and an open distal end 234. An intermediate tubular member 236 circumscribes the cartridge tubular member 230 and is positioned between tubular member 230 and an outer tubular member 242. A proximal end of the intermediate tubular member is secured to a collar 238. The intermediate tubular member 236 includes at least one pair of expandable curved arms 240 at its distal end which can be configured in accordance with the type of suture tie device used. The outer tubular member 242 is provided with a proximal end that is secured to a collar 244, and a distal end that is configured as a fixed, hook-like cradle 246. The cradle has a generally U-shaped or C-shaped cross-sectional configuration and terminates at a sharp point 248. A U-shaped handle 250 comprising distal and proximal arms 252 and 254 joined to one another by a curved spring portion 255 is arranged such that a distal arm 252 is secured to collar 244 and a proximal arm 254 is secured to collar 238. Ring handles 256a and 256b can optionally be provided along arms 252 and 254, respectively, to facilitate handle grasping and operation. A second curved spring member 258 connects collar 238 with a collar 259 that is secured to tubular member 230 of the cartridge 228 such that the inner tubular member 230 and intermediate tubular member 236 can move together to move the curved distal end 240 of the cartridge not only to distally advance the locking/tying member of the suture tie device, but optionally to move or manipulate the proximal portion of the suture tie device leg for a severing action or to hold or manipulate the locking/tying member at a desired position. A finger grip 260 extending downwardly from the collar 259 and spring member 258 can optionally be provided to facilitate spring member manipulation.

In use, a cartridge 228 housing a plurality of suture tie devices is loaded in the applicator 226. In order to position the distal-most suture tie device within the cradle 246, spring member grip 260 and arm 254 of handle 250 are urged toward one another, thereby moving tubular member 230 distally relative to intermediate tubular member 236, causing distal end 234 to open or expand arms 240 and allowing the spring bias within the cartridge to push the distal-most suture tie device beyond the expanded arms 240 and into cradle 246. When the grip 260 is released, the curved arms 240 return to their rest, generally closed position due to the bias from spring member 258 to restrict further distal movement of the remaining suture tie devices in the applicator. Once a suture tie device has been positioned within the cradle, the desired tissue or organ structure can be sutured by penetrating the tissue with at least one of the sharp distal ends of the hook-like cradle and the suture tie device in a conventional suture needle-like fashion. After penetration of the tissue, arms 252 and 254 of handle 250 are urged toward one another to an extent selected by the user, thereby moving intermediate tubular member 236 distally relative to outer tubular member 242 and causing the ends of curved cartridge arms 240 to move the locking/tying member distally so as to accomplish the suture tying function at a desired level of suture tension. Once the suture tying function has been completed to a desired level of tension, the handle 250 is released and the applicator is maneuvered so as to allow the tied suture tie device to be released from the applicator 226. Since a plurality of suture tie devices are preferably supplied in the cartridge, continuous (i.e., sequential and uninterrupted) suturing procedures can be accomplished without withdrawing the applicator from the surgical suture site.

FIGS. 27 and 28 illustrate an applicator 286 that represents a modification of the applicator 226 depicted in FIG. 25, in which similar components have been provided with identical reference numbers. As shown in FIG. 28, an inner cartridge tubular member 272 is provided having a curved distal end 274. As an alternative to the curved spring member 258 of FIG. 25, a spring-loaded cylinder 255 is provided which extends proximally from collar 238 to a shoulder 257 which is positioned adjacent to shoulder 273 of the inner cartridge tubular member 272 and houses a coiled spring 290 or other suitable biasing means. The cylinder 255 functions in a manner similar to the curved spring member 258 of applicator 226 by providing a means for displacing the inner and intermediate tubular members together distally. It will be appreciated, therefore, that the respective cylinder 255 and spring member 258 configurations can be interchangeable for applicators 226 and 286.

Illustrated in FIG. 29 is an applicator 262 that represents a further modification of the applicator 226 depicted in FIG. 25 that is particularly useful for adjusting the separation distance between the curved distal portion of various tubular member configurations for severing or manipulating protruding proximal portions of suture tie devices after suturing and tying. Throughout the following discussion of applicator 226, parts thereof which correspond to parts of applicator 262 are identified by like reference numerals and are not repetitively described. The spacing adjustment mechanism of applicator 262 is provided to control the spacing between the ends of curved arms 240 of the intermediate tubular member 236. The spacing adjustment mechanism 266 includes a threaded rod 268 having an end secured to the distal portion of curved spring member 258 adjacent collar 238. The rod 268 extends through a passage 258a formed in the proximal portion of spring 256 to protrude therefrom and threadably receive an adjustment nut 270.

Operation of the applicator 262 is implemented by squeezing the handgrip 260 relative to arm 254 of handle 250, thereby advancing the distal-most suture tie device into position in the cradle 246 in the manner described above with respect to applicator 226. The curved arms 240 return to their locking/tying member-pushing position when the grip 260 is released. Suturing can be accomplished in a manner similar to that obtained from use of a conventional curved suture needle, in which the tissue is penetrated by a curved insertion motion of the distal end of the applicator 262. Rigid tethers 264 connect the distal end 234 of the cartridge tubular member 230 with the distal end 240 of the intermediate tubular member. Distal and proximal movement of the cartridge tubular member 230 effects approximation and withdrawal, respectively, of the distal tips 271 by way of the tethers 264. Following tissue penetration by one or both of the cradle 246 and suture tie device, nut 270 of the spacing adjustment mechanism can be rotatably adjusted until it reaches the proximal end of the threaded rod 268, thereby urging distal curved arms 240 towards one another to position the distal ends 271 thereof in close proximity to one another to, for example, grasp the end of the length of suture material, abut the proximal end of the plug of a suture tie device, or to grasp and/or sever the proximal portion of any other various type of suture tie device such as those shown in FIGS. 1-20. With the distal ends 271 thus positioned, the handle arms 252 and 254 can be grasped and squeezed toward one another such that the distal ends 271 can, for example, push the length of suture material distally toward the tissue penetrating leg 150 in instances where the suture tie device 148 of FIG. 18 is utilized. Following the completion of any adjustment to the relative spatial arrangement of the distal ends 271, the nut 270 is rotated back to its rest position to open the distal ends 271 and return them to their locking/tying member-pushing position. Handle 250 can then be squeezed further together to advance the locking/tying member distally to complete the tying operation. Once the tying operation has been completed, the handle is released and the tied suture tie device can be released from the applicator 262.

A further alternative arrangement for an applicator 277 that is a modification of applicator 262 of FIG. 29 is illustrated in FIG. 30, where parts of applicator 277 identical to parts of applicator 262 are provided with identical reference numbers. Applicator 277 is substantially similar to applicator 262, with the exception that applicator 277 includes a means 269' for positioning the curved distal end of the distal portions of the inner and intermediate members at a desired position for any severing, compressing, or manipulating action that may be required incident to the handling of a particular configuration and type of suture tie device used therewith. The positioning means 269' includes a rod 278 having a proximal end rotatably mounted to handle arm 254, a finger grip 280 at the distal end of the rod, and angled teeth 282 protruding from the rod along the length thereof. The rod 278 extends through an opening 279 formed in arm 252 of the handle and is operable in cooperation therewith to lock the position of the handle arms 252 and 254 in a predetermined spatial relationship. In use, the rod 278 can be rotated and locked in position to allow precise positioning of the distal ends 271 of the curved arms 240 of the tubular member 236 prior to the aforedescribed severing operation. Once a suture tie device has been advanced distally into the cradle 246, as by grasping and squeezing toward one another grip 260 and handle arm 254, the tissue or organ structure can be penetrated by at least one of the distal ends of the suture tie device and cradle. Following penetration of the tissue or organ structure to be sutured, the handle 250 can be squeezed to direct movement of cartridge arms 240 to move the locking/tying member distally to accomplish the tying function. After tying, the handle 250 can be manipulated so as to position the distal ends 271 along the proximal portion of the suture tie device to the desired position for severing the proximal portion of the suture tie device, and the position of the handle 250 can be fixed by rotatably adjusting the position of the rod 278 so that the teeth 282 can engage the handle opening 279. The nut 270 of the spacing adjustment mechanism 266' can be rotated until it abuts ring handle 284, thereby directing rigid tethers 264 to pull arms 240 together to sever the proximal portion of the suture tie device at the desired point. Thereafter, the rod 278 can be released, and the screw 270 moved back to its rest position to permit the tied suture tie device to be released from the applicator.

As mentioned above, there are various configurations for the distal portions of the inner and intermediate tubular members which can be utilized with the applicators discussed above for applying the various suture tie devices of FIGS. 1-20. For example, FIG. 31 shows the inner tubular member 272 as having a distal curved portion 274 that is provided with sharp severing ends 273, and the intermediate tubular member 276 as having a blunt distal end. The distal portion 274 can be provided with a variety of configurations as well so as to accommodate the structure of the specific suture tie device to be used. FIG. 32 shows a distal face 240' for pushing the locking/tying members of a wide variety of the various suture tie devices shown in FIGS. 1-20. The distal face includes an indented portion 241' which can be provided with a sharp severing edge for severing the proximal portion of the legs after the tying process is complete. FIG. 33 shows the distal face 240" which is arranged to push the locking/tying member specifically of suture tie device 148 after distal face indentations 241" engage and advance the suture material 154 or 154' distally to circulate through the leg 150 of the device 148. These indentations 241" can also be provided with a sharp edge for severing the protruding proximal portion of the suture material. The central indentation 241' can include a severing edge which allows the configuration of FIG. 33 to also be used with various other suture tie devices of FIGS. 1-20.

FIG. 35 illustrates an arrangement in which an inner tubular member 230' is provided with a straight distal portion with longitudinal slots 265' for allowing the distal and proximal movement of the curved distal portions 240' of intermediate tubular member 236'. As the inner member 230' moves proximally, the distal tips 271', if sharpened, provide a severing action, and if blunt, provide a grasping, manipulating and/or compressing action. The distal blunt ends 233' can be positioned specifically for the suture tie devices of FIGS. 16-20. Indentations 231 can be shaped to accommodate either the curved needle portion of the various suture tie devices or the various locking/tying members, and can be disposed along the inner surface of the innermost tubular member of any of the configurations described for the various applicators. These indentations can function in a manner analogous to the guides 224 depicted in FIGS. 24B and 24C to hold and space apart accordingly the suture tie devices within the cartridge.

With reference to FIGS. 36A and 36B, there is depicted a multiple leg suture tie device 300 in accordance with a further aspect of the present invention. The suture tie device 300 is comprised of at least two generally opposed and elongated tissue engaging or penetrating legs 302 and 304 and a locking/tying member 308 which at least partially surrounds at least one, and preferably all, of the legs 302 and 304. The legs 302 and 304 are preferably joined at their respective proximal ends at a common proximal base 306 to facilitate handling of the device 300. The multiple-leg suture tie devices can be partially or entirely made of entirely or partially bioabsorbable or non-bioabsorbable material, as is the case of their single leg counterparts discussed above, and can also be provided with appropriate physical characteristics in accordance with their intended utilization and site of application. For example, either or both of the locking/tying member 308 and legs 302 and 304 can be configured so as to be entirely or partially rigid, semi-rigid, flexible, elastic, resilient, or malleable. The distal ends 400a and 402a of the legs 302, 304 are configured so as to interlock with one another or abut against one another in close proximity and are preferably angled or curved toward one another to facilitate suture tie device closure in the manner described below. Appropriate interlocking means can be provided along one or both of the legs to interlock the legs incident to suture loop formation. For example, leg 302 can be provided with a hollow female-like tubular distal end 400a having a bore or lumen 401a formed therein to receive the probe-like male distal end 402a of leg 304. This hollow end can be provided with a sharp or blunt edge, and can be provided with a substantially closed, generally annular cross-sectional configuration. A plurality of perforations or holes 321 extending through the wall at the distal end of leg 302 can be provided to communicate with lumen 401a. The distal end 402a of leg 304 defines a tissue-penetrating male member adapted to be received in the hollow distal end 400a of leg 302 such that locking protrusions 323 such as knobular extensions or ridges of distal end 402a can extend into perforations 321 of distal end 400a to lock the male probe member within the female tubular member. The configurations of the leg interlocking means described above can be replaced with any other suitable configuration that ensures secure engagement of the leg members upon leg engagement. It is to be appreciated that the legs of suture tie device 300 can be provided with a greater or lesser degree of curvature than that depicted in FIG. 36A, as illustrated in the further suture tie device arrangements depicted in the drawings and discussed below.

The locking/tying member 308 of the device 300 defines a central lumen or passage 310 through which the legs extend. The interior of the central lumen 310 is configured with appropriately sized recesses or deformable walls to accommodate the curvature of the distal portion of legs 302 and 304 when the locking/tying member is advanced in the distal direction following superposition or interlocking of the distal ends 400a and 402a to create a suture loop. Alternatively, one or both of the legs can be moved toward the other leg by distal advancement of the locking/tying member 308 over the exterior surface of at least one of the legs 302 and 304. The locking/tying member 308 can optionally be provided with internal coupling means 309a such as angled teeth (FIG. 36B) along the interior surface of the central passageway 310 for cooperating with complementary means 339b such as a plurality of angled teeth or barbs protruding from the outer surface of the legs 302 and 304 for providing selective displaceability of the locking/tying member 308 in a predetermined single (distal) toward the distal ends 400a and 402a of legs 302 and 304, respectively. Other suitable coupling means can be substituted for the arrangement of complementary angled teeth 339a and 339b to provide the desired control over the direction of movement of the locking/tying member in relation to the legs of the device, examples of which means include whisker-like filaments, ridges, angled pins, and microholes, all of which can provide for one-way displaceability of the locking/tying member and can be disposed along all or part of the entire surface of one or more of the legs and the lumen of the locking/tying member. The locking/tying member directional displacement controlling means 339b, such as the array of angled teeth or barbs depicted in FIG. 36B, can be replaced by radially-extending filaments or other suitable means which allows for bi-directional displacement of the locking/tying member 308 along the legs 302 and 304. Such a bi-directional enabling arrangement can be advantageous in certain surgical procedures where it would be desirable to permit the suture tie device user to loosen tension in the suture loop in the event that the tissue or organ structure interposed between the legs 302 and 304 has been inadvertently over-tensioned by manipulation of the locking/tying member distally in excess of the distance necessary to provide optimal suture loop tension.

In use, the suture tie device 300 is preferably mounted in a needle-like or forcep-like member of an applicator similar to that disclosed in the abovementioned patent application, Ser. No. 049,504, and to those shown in FIGS. 52, 53 and 61 herein, and the suture tie device is manipulated in a manner similar to that associated with manipulation of a conventional suture needle. That is, one or more of the needle points formed by the distal ends 402a and/or 400a is maneuvered to cause the tips thereof to penetrate sections of tissue to be sutured. Penetration of the tissue can be accomplished by a single tip entering at least one of the tissue sections first, or by all of the tissue sections being penetrated substantially simultaneously, or can be accomplished by the distal tips of the applicator in the manner described below. Once the suturing penetration maneuver is completed, the applicator can be operated to move penetrating legs 302 and 304 relative to each other to cause the male member formed by the tip 402a to be received within the female member formed by distal hollow end 400a and locked therein due to the engagement of protrusions 323 with holes 321. Alternatively, the tissue to be secured by the suture tie device can be sutured by movement of one or both of the legs 302, 304 toward the other such that the respective leg tips 400a, 402a are brought into opposition with one another so as to abut against one another or nearly contact one another with a relatively small separation space therebetween. The locking/tying member 308 can then be moved distally along the legs 302 and 304 to create a desired tension in the suture loop formed by interlocking on approximation of the legs 302 and 304. That is, the locking/tying member 308 operates in a substantially similar fashion as a knot tied in a conventional length of suture material and can thus be moved along the penetrating legs 302 and 304 to variable positions in accordance with the desire of the surgeon to variably compress the tissue together by controlling the tension on the suture loop formed by the penetrating legs and the locking/tying member. Once the locking/tying member is properly positioned, the portion of the suture tie device 300 extending proximally beyond the locking/tying member can be severed at a desirable position and, if formed from a bioabsorbable material, can be left at the surgical site to be absorbed by the body. Interlocking of the distal ends of the penetrating legs 302 and 304, in combination with the flexibility of the legs, allows the suture tie device 300 to lie substantially flat against the sutured tissue without disengaging. Accordingly, it will be appreciated that the suture tie device 300 utilized with the applicator permits relatively simple and expedient sequential suturing of tissue, as shown in FIGS. 50A through 50C during open or closed (endoscopic) surgical procedures, thus substantially reducing the time required for the completion of such procedures and allowing for the use of endoscopic instrumentation in instances where it otherwise may not have been feasible.

A further embodiment of a suture tie device according to the present invention is illustrated in FIG. 37, wherein a plurality of elongate tissue approximating or penetrating legs 332, 334, 336 and 338 are provided which extend from a proximal end 340 of the suture tie device 330. The legs are preferably arranged in opposed pairs, although an uneven number of legs can be provided, and the legs can be independently or simultaneously manipulated in accordance with the intended use of the suture tie device. The multiple leg suture tie device 330 can be utilized for various procedures, such as closing anatomical lumens or for joining multiple separated sections of tissue, and can be utilized in an applicator having a plurality of forcep-like or needle-like members equal in number to the number of tissue approximating or penetrating. Operation of the device 330 is similar to that described above in connection with application of the device 300. Once the distal ends of the legs have been moved to the desired positions, the locking/tying member 308 is moved distally to tension the suture loops formed by each pair of opposed suture legs, thereby causing the anatomical lumen to be reduced in diameter or closed off. As is the case with the suture tie device 300 described above, the distal ends of the penetrating legs of the multi-legged device 330 can be provided with a wide variety of configurations to allow approximation or interlocking thereof as depicted in FIGS. 43A through 43F, and can be provided with a plurality of angled teeth or barbs 327 for engaging a conical or cylindrical bore 310 formed in the locking/tying member 308 to permit movement of the locking/tying member in only the distal direction toward the distal ends of the legs. It will be appreciated that the coupling means 339 for controlling movement of the locking/tying member along the respective device legs can vary as described above for all suture tie devices, whether they have single, double, or multiple-legs. Once the locking/tying member 308 has been moved to produce the desired tension in the suture loops formed by the two opposed pairs of legs, the protruding proximal portion of the suture tie device 330 can be severed as described above.

A further alternative aspect of the multiple leg suture tie device according to the present invention is illustrated in FIG. 38, in which the suture tie device 350 is provided with distal portions 368 and 370 of legs 352 and 354, respectively, which are relatively sharply curved so as to create a generally circular cylindrical space for retaining a segment of tissue therein. The curved portions 368 and 370 of the legs 352 and 354 are preferably angled with respect to the proximal portion of the legs so that the distal tips extend generally transversely therefrom and are accommodated by recesses 374 and 378 formed within the locking/tying member 372. As described above, coupling means 339 such as ridges or barbs can be provided along the length of the legs 352 and 354 and within the passage 310 of the locking/tying member 308 to allow only for the distal movement of the locking/tying member therealong. The configuration for the interlocking means of the distal ends can vary as shown in FIGS. 43A through 43F and described below. The suturing procedure for use of the device 350 is substantially similar to that described above for suture tie device 300.

FIG. 39 illustrates a further modification of a suture tie device according to the present invention, in which the suture tie device 410 is provided with tissue penetrating legs 412 and 414 which are generally rectilinear in configuration and can optionally be provided with slightly umbilicated spaces at their distal portions for suturing additional quantities of tissue. The angled distal ends can be especially useful for tubal ligation, vasoligation, or ligation for any other floating or unfixed tubular structure. Male and female distal portions 415 and 417 extend generally transversely from penetrating legs 412 and 414, respectively, with the distal end 415 defining a cavity or recess 419 having a plurality of ribs 365 formed therein to co-act with frusto-conical protrusions 327 formed on the distal end 421 of the opposed leg 414 to lock the distal end 421 within the cavity 419 of the distal end 415. As noted previously, the female member can also be provided with a sharp edge to penetrate the tissue substantially simultaneously with the male member upon manipulation of the legs toward one another. It is to be appreciated that the configurations of both the legs of the suture tie device and their respective distal ends can be varied in accordance with the type of tissue to be sutured and the location of the suture site within the body of the patient.

A further modification of a suture tie device of the present invention is illustrated by suture tie device 430 in FIG. 40. In contrast to the structure and manner of intended operation of the suture tie device 410, the penetrating leg 432 is arranged to be stationary, with only penetrating leg 432 being displaceable by the applicator to interlock the distal ends 400c and 402c. An indentation or score line 433 can be provided along leg 432 to facilitate folding of the leg toward stationary leg 434. The proximal portion of the legs can terminate at a common base 306, or they can be arranged as separate, discrete members throughout their length, as can be the case with any of the multiple-leg suture tie devices described above and depicted in FIGS. 36A through 39. The open female member distal end 415' is provided with a plurality of internal ribs 459 (depicted in phantom) to interlock with frusto-conical protrusions 327 of the male member distal end 417' and a passage 419' having a slot 453 formed therein to receive the male member distal end. An aperture 451 is formed at the leg bend 438 of the distal end 400a to receive therethrough the sharp tip of the distal end 402c of the male member 417' incident to interlocking of the legs 432 and 434. Following leg interlocking, locking/tying member 308 can be advanced distally to obtain a desired degree of tension in the suture loop in the manner described above.

FIG. 41 illustrates a suture tie device 470 which illustrates a further variation of a suture tie device in accordance with the present invention, and particularly the single displaceable leg arrangement depicted in FIG. 40 and discussed above. Displaceable leg 472 is arranged to be received in an appropriately-dimensioned channel 511 formed in the opposed stationary leg 474. The leg 472 is sharply angled at bend 478 to form a distal end 415" that extends generally transversely from the leg. The distal end 402d is provided with a plurality of outwardly-extending ribs or ridges 459' along its distal surface that are adapted to be received by correspondingly-dimensioned recesses 461 formed in the distal surface of the distal end 417" of the stationary leg 474. The tips 400d and 402d of the distal ends 415" and 417" can be provided with sharp edges to facilitate tissue piercing. Additionally, the stationary leg 474 is preferably provided with a recess 455 formed adjacent the bend 480 for receiving therein tissue that is interposed between the legs 472 and 474. Preferably, the stationary leg 474 is provided with a plurality of slots or grooves 505 along the length of the leg to embrace corresponding protruding members 473 (FIG. 42) such as ridges, teeth or barbs formed along the leg 472 when the leg 472 is urged into cavity 511. The proximal end of leg 474 terminates in a sleeve 482 which is provided with a lumen 484 to accommodate the proximal portion 476 of leg 472. The arrangement of mutually engageable leg protruding members 473 and grooves 505 is provided in lieu of a displaceable locking/tying member as an alternative means for adjusting tension in the suture loop created by approximation or engagement of the distal ends of the respective legs 472 and 474. The desired degree of tension in the suture loop can be obtained by engaging an appropriate number of corresponding leg protruding members and grooves upon pivotable displacement of leg 472 with respect to leg 474.

Various modifications of distal end configurations for use with the suture tie devices depicted in FIGS. 36A through 38 and described above are illustrated in FIGS. 43A through 43F, in which similar components are identified by like reference characters. It is to be understood, however, that the illustrated modifications are merely exemplary of the myriad of possible distal end configurations and that the specific configuration utilized with a suture tie device will depend upon the type and location of tissue to be sutured, extent of the manipulation required to effect suturing, and the preference of individual surgeons. In accordance with the type of tissue for which the suture tie device is to be utilized and the objectives of the surgical procedure, the distal ends of the device can be configured so as to interlock, engage, or simply to approximate one another, the distal ends can be or arranged such that one end is received within the distal end of the other leg. The distal tip of one or both of the mutually cooperable distal ends can be configured as a sharp, tissue-penetrating distal end, whereas the other of the distal ends can be configured as a blunt end. Alternatively, both mutually cooperable distal ends can be configured as blunt ends, as may be desirable when the distal ends are to be positioned in close proximity to one another but not engage or interlock. It shall be appreciated that depending on which suture tie device is utilized, the distal ends will be shaped accordingly.

With reference to FIG. 43A, the distal end 402a of the leg 304a is provided with a sharp tissue-penetrating distal edge and includes a plurality of protrusions 323. The distal end 400a of leg 302a is configured to be received within a bore or lumen 401a of a female distal end 400a, which is provided with a plurality of the perforations 321 for locking engagement with the protrusions 323 of the male member 402a upon insertion of the distal end 402a therein.

With reference to FIG. 43B, a sharp male distal end 402b of leg 304b is provided with a plurality of conical protrusions 327 and is arranged to be received within the lumen 401b of the female distal end 400b of leg 302b. The interior surface of the lumen 401b is provided with a plurality of rib-like protrusions 325 which extend into the lumen 401b to interlock with the conical protrusions 327 of the male member.

FIG. 43C illustrates a distal end arrangement in which a sharp male distal end 402e is provided that includes an arrangement of conical protrusions 327. The female distal end 400e defines an undersized cavity 401e and is split by a generally V-shaped slot 403 into a pair of opposed, longitudinal portions 404e and 405e having a plurality of inwardly-extending ridges or protrusions 325 formed along the respective interior surface. Separation of the female distal end 400e into longitudinally opposed sections in the manner described above provides the distal end 400e with a spring-like bias to permit receipt of the male member 402e. The inwardly-extending ridges or protrusions 325 of the female member 400e can interlock with ridge-like protrusions 327 formed along the exterior of the male member. The provision of a spring-biased female member and the arrangement of interlocking protrusions 325 and 327 carried by the respective female and male members ensures secure interlocking engagement of the distal ends of the suture tie device.

Figures 43D, 43E, 43F:
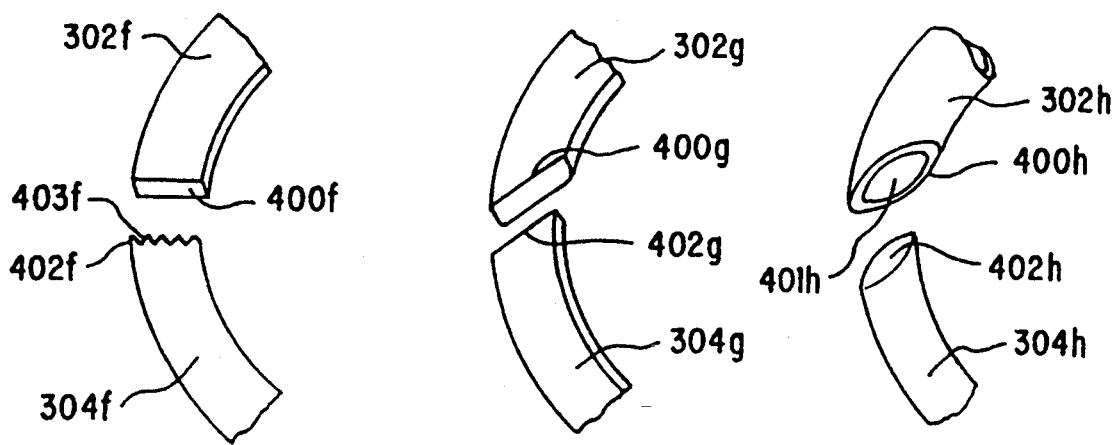

FIGS. 43D and 43E illustrate arrangements for suture tie device distal ends in which the distal ends are to be positioned in close proximity with one another but not physically engage or interlock. With respect to the arrangement depicted in FIG. 43D, the distal ends 400f and 402f of legs 302f and 304f, respectively, are arranged so as to be positionable in a generally parallel orientation that is generally parallel to the longitudinal axis of the suture tie device. At least one of the distal ends, such as distal end 402f, can be provided with a plurality of jagged teeth 403f to facilitate tissue penetration. FIG. 43E illustrates an arrangement similar to that depicted in FIG. 43D, with the exception that the distal ends 400g and 402g are positionable generally parallel to one another along a plane that extends generally non-transversely of the ends of corresponding legs 302g and 304g. It will be appreciated that one or more of the pairs of distal ends 400f, 402f and 400g, 402g can be configured as sharp or blunt ends, and can be configured as generally planar ends as shown, or as non-planar, jagged sharp or blunt ends in accordance with such factors as the type of tissue to be sutured and the preference of the user.

FIG. 43F illustrates a distal end arrangement in which the distal end 400h of leg 300h defines a lumen 401h that is dimensioned to receive in non-interlocking fashion the solid distal end 402h of opposed leg 304h. Mechanical interlocking means such as ridges, barbs, slots and other arrangements as discussed above are not provided with either of the distal ends of this arrangement. Instead, the legs 302h and 304h of the suture tie device are secured in position by receipt of the distal end of one of the legs within the lumen defined by the other of the opposed pair of legs.

Further modifications of the distal end configurations for use particularly with suture tie devices depicted in FIGS. 39 through 41 are illustrated in FIGS. 44A through 45D, the illustrated modifications being exemplary and not limiting. With reference to FIG. 44A, the male distal end 415'a terminates at a sharp distal tip 419'a and includes a plurality of conical protrusions 327 formed along its exterior surface. The distal end 417'a of the opposed leg is curved so as to extend proximally and terminate at a sharp distal tip 540a. An aperture 541a is provided adjacent the tip 540a that is dimensioned to receive, and optionally engage, the distal end 415'a and the conical protrusions 327 carried thereby- Interlocking protrusions (not shown) such as the protrusions 325 depicted on FIG. 43B and described above can optionally be provided along the interior surface of the aperture 541a.

FIG. 44B illustrates a distal end arrangement in which the sharp male distal end 415'b extends from the leg so as to define an acute included angle a and is provided with a plurality of angled or conical protrusions 327. The distal end 415'b is configured so as to be received within a recess 541b formed in the opposed female distal end 417'b. The female distal end 417'b includes a plurality of barbs or ridges 365 formed along the interior of the recess 541b to interlock with protrusions 327 of the male member 415'b. The barbs or ridges 365 are preferably arranged in opposed rows, as shown in the drawing, although other configurations can be provided. Shoulders 418 and 420 are provided adjacent the distal ends of the respective legs 432 and 434 are provided to inhibit distal movement of the locking/tying member beyond the distal ends of the suture tie device.

Further distal end configurations for the legs of the various suture tie devices depicted in FIGS. 36 through 41, and most notably FIGS. 40 and 41, are depicted in FIGS. 45A through 45D. With reference to FIGS. 45A and 45B, there is depicted a leg distal end arrangement 550a in which the lower leg 434, which can either be fixedly positioned or movably mounted to the proximal end of the suture tie device, is provided with a curved configuration which terminates at a proximally-extending sharp tip 554a. The lower leg 434 can optionally be provided with a recess 455 adjacent the curved distal end for accommodating tissue sutured by the suture tie device. The distal end 552a of the opposed leg 432 terminates at a sharpened tip 556a that is curved so as to extend beyond the distal-most edge of the distal end 550a. A slotted aperture 501 is provided adjacent distal end 552 along arm 432 to receive the curved distal end 550a of the opposed arm 434 therethrough.

FIG. 45C depicts a distal end arrangement in which a male distal end 552b of one of the legs of the suture tie device, such as leg 432, is provided with a sharp distal tip 556b and an inwardly-extending notch or recess 503 formed along the distal edge of the end 552b. Opposed female distal end 550b of leg 434 is configured so as to curve toward the male distal end 552b and terminates at a sharp tip 554b. The distal end 550b includes an aperture 555 formed along the associated leg of the suture device that is appropriately dimensioned to provide for an interlocking engagement with the recess 503 of the opposed distal end 552b.

FIG. 45D depicts a further distal end arrangement in which the distal end of one of the legs, such as distal end 552c of leg 432, is provided with an outwardly-extending protruding member 505, and the distal end 550c of the other leg 434 is provided with a plurality of aligned recesses 503, each of which is dimensioned to receive the protruding member 505 of the opposed leg 432. Tissue receiving recess 455 as described above can optionally be provided along the leg 434, as shown in the drawing. The arrangement of recesses 503 allows the suture tie device to be used in conjunction with a relatively wide variety of tissue thicknesses, as engagement of the protruding member 505 with a selected one of the plurality of recesses permits the user to select the appropriate extent of distal end engagement that may be desirable for a particular utilization of the suture tie device. Whereas the depicted distal end arrangement provides for the protruding member to be positioned along the distal side of the distal end 552c and fort he plurality of recesses 503 to be positioned along the proximal side of distal end 550c, it is to be appreciated that the placement of the protruding member and recesses could be reversed from that depicted. Additionally, the respective distal end configurations could be reversed from that shown in FIG. 45D, such that distal end 552c is provided on leg 434 and distal end 550c is provided on leg 432.

Details of specific configurations for the surfaces of the legs of the various suture tie devices described above are depicted in FIGS. 46 and 47 for coupling with the corresponding surface of an opposed leg or with the interior luminal surface of the associated locking/tying member. With reference to FIG. 46, the inwardly-facing surfaces of each leg, such as leg 304, can be provided with a plurality of ribs 562 and grooves 563 arranged in an alternating configuration to facilitate mating cooperation and locking between the legs of the suture tie device when the leg surfaces are superposed over one another upon distal movement of the locking/tying member. The ribs 562 and grooves 563 can be oriented so as to extend longitudinally along the length of the legs. Alternatively, the ribs and grooves can be oriented in any of a variety of configurations, such as laterally or angularly extending with respect to the longitudinal axis of the leg, with the ribs and grooves on the other leg having a corresponding configuration to facilitate mating thereof.

FIG. 47 illustrates an enlarged segment of a leg of a suture tie device 410 as described above in connection with FIG. 39 illustrating one configuration of the coupling means 339b in which a plurality of ridges 560 are formed within a longitudinal groove 564 which extends along the length of the leg. The ridges 560 are configured Go couple with a corresponding internal luminal configuration 339a of the locking/tying member 308 to provide the desired degree of uni- or bi-directional control of locking/tying member displacement along the respective legs of the suture tie device.

FIGS. 48A and 48B illustrate the use of a suture tie device of the subject invention, such as the device 300 depicted in FIG. 36, for occlusion of an anatomical tubular organ structure such as a Fallopian tube or vascular member 282. Because of the curved configuration of the legs 302 and 304, the suture tie device 300 can easily be utilized with comparatively large tubular members by virtue of the adjustability in capacity and size for the suture loop that can be created by the device 300. As shown in FIG. 48A, the suture tie device 300 can be manipulated by an appropriate applicator (not shown) so as to position the tubular member 282 between the opposed legs 302 and 304 of the device. One or more of the sharp distal ends 400b and/or 402b of the legs 302 and 304 can be manipulated to penetrate the tubular member supporting membrane 280, after which the leg distal ends can be displaced relative to one another so as to approximate, engage or interlock in the manner described above to form the suture loop, designated generally by reference character L. Leg approximation, engagement or interlocking can be accomplished by either displacing one or both of the opposed legs toward the other as described above and then distally advancing the locking/tying member to obtain the desired degree of tension in the suture loop, or by distally advancing the locking/tying member in the absence of any prior movement of the distal ends of the legs so as to displace one or both of the opposed legs to approximate, engage or interlock with the other. The position of the locking/tying member 308 along the device legs 302 and 304 is maintained by the cooperation of leg-engaging means 339a (FIG. 36B) provided along the lumen 310 of the member 308 and the arrangement of barbs/angled teeth 339b or other suitable means, such as ribs 562 (FIG. 46) and ridges 560/grooves 564 (FIG. 47). When the suture tie device 300 is formed entirely from bioabsorbable material, the suture loop L formed by the device 300 can remain in place until the device is absorbed into the tissue surrounding the tubular member. It will be appreciated that the time period before which absorption is completed can be varied in accordance with the selection of material used in the device and the dimensions and configuration of the device and all of its components. Excess suture material proximal of the locking/tying member 308 can be trimmed from the device 300 along the line "S", if so desired by the user.

FIGS. 49A through 49C illustrate use of a suture tie device 330A in its representative suturing stages as described above. The device 330A is a modification of the suture tie devices 300 and 330 described above, in which the suture tie device 330A is provided with two of the four opposed legs of the device 330 shown in FIG. 37. With reference to FIG. 49A, the segments of tissue 284 and 286 are penetrated by either one or both leg distal ends 400b and 402b with or without the assistance of the forcep-like or needle-like members of the applicator described below, and the distal ends are moved toward one another so as to interlock. Interlocking of the distal ends of the legs, as shown in FIG. 49B, permits the tissue segments to be joined and further sutured by the tying of the suture loop by way of distal movement of the locking/tying member 308. Following appropriate tensioning of the suture loop L by movement of the locking/tying member distally along the legs 332 and 336, as illustrated by the arrows. In a preferred aspect of the invention, the entire suture tie device 330A is in FIGS. 49A and 49B, the protruding proximal portion of the suture tie device can be severed at a desired position, as indicated by the dotted-line S of FIG. 49B, and removed from the surgical site to provide a neatly trimmed suture loop L (FIG. 49C) at the suture site. Tensioning of the suture loop L can result in a slight bending of the leg distal ends in a proximal direction toward the locking/tying member, thereby further securing the tissue segments 284 and 286 within the suture loop L formed from a suitable bioabsorbable material in order to permit the suture loop and any severed portions of the suture tie device to remain at the surgical site to be absorbed by the tissue.

The suture tie devices of the subject invention can also be used to close or substantially close a tissue aperture, as noted above. The multi-leg pair suture tie device 330 of FIG. 37 is most advantageously used for aperture closing. With reference to FIG. 50, the distal ends 400b, 400b and 402b and 402b of the legs 332, 334, 336 and 338 are positioned adjacent the aperture "A" in tissue segment 285 and are extended into the tissue segment. The distal ends of the respective leg pairs can optionally be interlocked with one another. Following penetration of the tissue segment 285 by the legs, the locking/tying member is distally advanced in the manner described above to reduce the size of the suture loops extending between each opposed leg pair and the locking/tying member, thereby reducing the dimensions of the aperture "A".

While the foregoing description has described the use of the various arrangements of suture tie devices for closed surgical procedures at surgical sites typically remotely situated from the exterior surface of the body of a patient, it is nevertheless to be understood that the suture tie devices of the present invention are likewise applicable for use in subcuticular suturing to close an opening or wound in the skin of a patient. Subcuticular suturing can be accomplished by manipulating one or more suture tie devices of the subject invention so as to penetrate only the subcutaneous layer of the skin to close or substantially close the wound or opening with a minimal amount of contamination to decrease the incidence of infection, facilitate healing, and minimize the formation of scar tissue. Depending on the location of the surgical site, various shapes and sizes of suture tie devices can be utilized. It is to be further understood that both macro and micro-surgical procedures can be accomplished through the use of suture tie devices of various dimensions and configurations of the subject invention.

Figure 51:
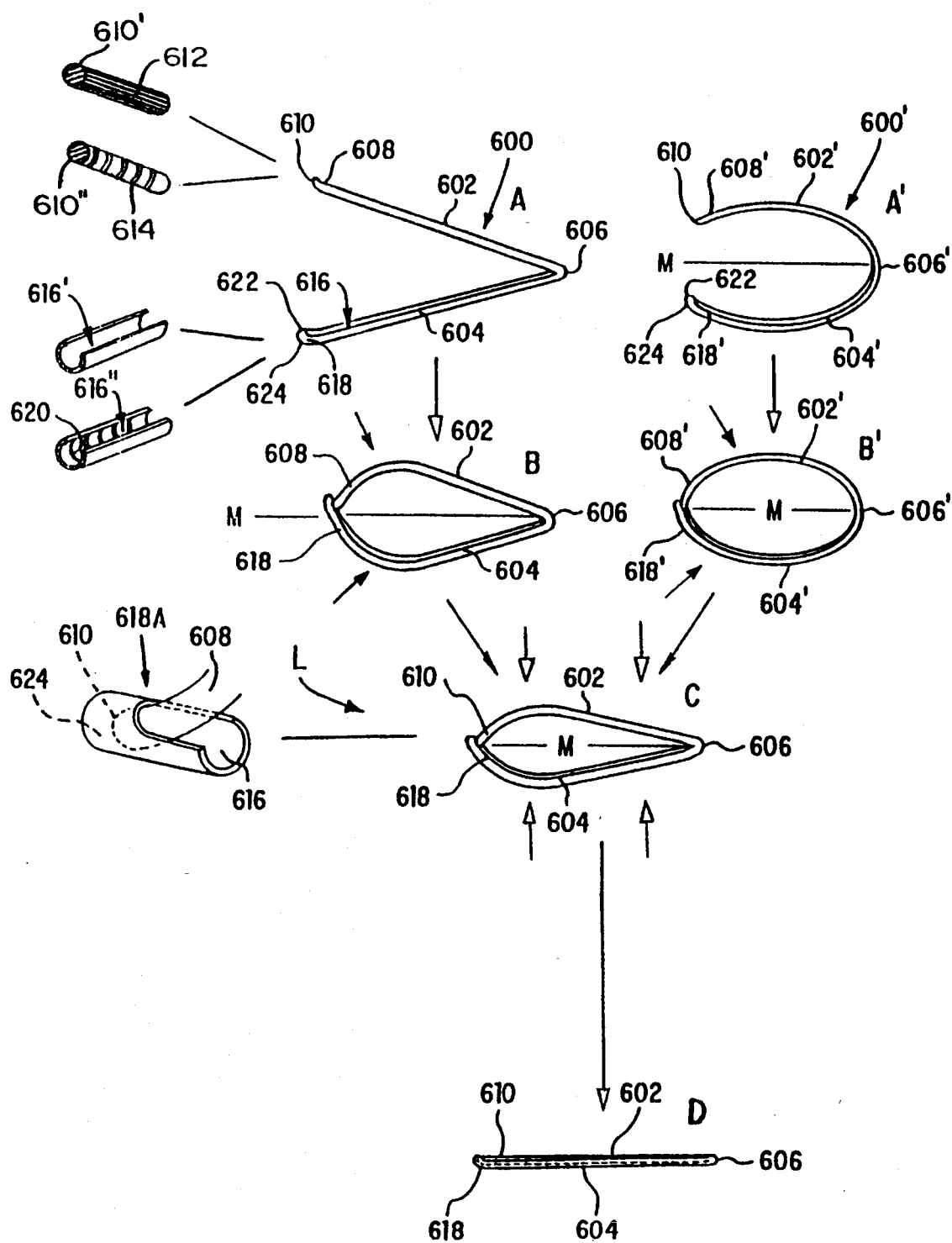
FIG. 51 illustrates sequential operation of a further alternative suture tie device in accordance with the subject invention.

With reference to FIG. 51, there are depicted further alternative aspects of the suture tie devices of the subject invention and their respective operational sequences for effecting tissue approximation. The illustrated suture tie devices 600 and 600' are in the form of adjustably tensionable clip-like structures and can be formed from a surgical grade of stainless steel, titanium, or suitable bio-absorbable material. As shown in the drawing, the device 600 is comprised of a generally elongate member that can be configured into a pair of opposed legs 602 and 604 that are joined at their respective proximal ends at bend 606. The distal end 608 of the leg 602 terminates at a tip 610 that is axially aligned with the principal (longitudinal) axis of the leg 602 from which it extends. The tip 610 can optionally be provided with an array of outwardly and longitudinally extending ribs 612, as shown at 610', or the tip 610 can be provided with a plurality of outwardly extending ribs 614 that extend generally transversely of the longitudinal axis of the tip, as shown at 610". The opposed leg 604 defines a generally U-shaped or C-shaped channel 616 (when viewed in cross-section) that terminates at a closed-ended distal end 618. The channel 616 can be provided with a generally smooth interior surface, as shown at 616', or can be provided along its interior surface with a plurality of ridges or grooves 620 that extend generally transversely of the longitudinal axis of the leg, as depicted at 616". Regardless of the interior configuration of the channel, the channel can be resiliently biased to resiliently receive and retain the opposed leg member in the manner described below. The distal end 618 is preferably configured so as to bend toward the opposed leg 602 and terminate at a sharp distal tip 622. Because of the curvature of the distal end 618, the distal end defines a recess or pocket 624 for receiving and retaining the distal tip 610 of the leg 602 upon engagement of the respective distal ends 608 and 618 in the manner described below.

Step B illustrates the initial step of closure of the device 600, in which closure is initiated by extending one or both of the distal ends through the tissue to be joined and applying a force in the direction of the arrows against the distal ends 608 and 618 along an acute included angle with respect to the longitudinal mid-line M so as to bend the respective distal ends 608 and 618 toward one another so that the distal tip 610 of arm 602 is inserted within channel 616 of the leg 604 so as to engage with the distal end 618 of the leg 604. Once the respective distal ends have engaged one another in the manner described above, force is further applied to the respective exterior surfaces of the legs 602 and 604 in a direction generally transverse of the mid-line M, as indicated by the arrows in the Step C, so as to urge the distal end 610-into recess 624 of distal end 618. Alternatively, the clip 600 can be progressively collapsed following distal end engagement from the distal end toward the proximal end of the clip (i.e., from the left side toward the right side in the drawing) or from the proximal end toward the distal end in the manner described above with reference to the clip structure 470 (FIG. 41). The distal end of the leg 604 can be configured with a Sharp distal tip 622, as illustrated in Step A, or the distal end can be provided with a generally rounded blunt end, as indicated at 618A. As is shown in the detailed illustration of the distal end arrangement designated by reference character 618A, as force is exerted generally transversely of the mid-line M, the distal tip 610 of leg 602 is advanced distally within the closed recess 624 in the direction of the arrow in phantom to securely interengage the two respective distal tips 610 and 618. Further application of force transverse of the mid-line M brings the legs 602 and 604 into a generally parallel, superposed orientation, as indicated at Step D, with tissue to be secured by the device 600 interposed between the legs 602 and 604. Control of the application of force allows for tensioning of the suture loop L formed by the interengaged distal ends 608 and 618 and the connected proximal leg ends to a level selected by the user.

With reference to steps A' and B', there is depicted a further alternative configuration for the suture tie device depicted in Steps A through D. Step A' illustrates a device 600' that is comprised of a pair of generally opposed legs 602' and 604' that are joined together at their respective proximal ends at bend 606'. The leg 604 defines a generally U-shaped or C-shaped channel 616 that can be configured in a manner analogous to that of channel 616 of the device 600. The distal end 608' of the leg 602' is curved toward the longitudinal mid-line M and terminates at a distal tip 610. The distal end 618' is also curved toward the mid-line M, and defines a recess 624 that is continuous with the channel 616 for receiving the distal tip 610. The distal end 618' terminates at a distal tip 622 that can be configured as a sharp tip for facilitating tissue penetration, or as a blunt tip 618A. As force is exerted against the respective distal ends 608' and 618' along an acute included angle relative to the mid-line M (Step B'), the distal tip 610 is received within the channel 616. Thereafter, operation of the device 600' is identical to that for the device 600 and follows the procedure described above and illustrated in Steps C and D.

The suture tie devices 600 and 600' can be formed entirely from the same material, or they can be formed from different materials in accordance with the objectives of the surgical procedure and the nature of the tissue to be sutured. For example, one or both of the device legs can be formed entirely or partially of a rigid or semi-rigid bioabsorbable material or from a non-bioabsorbble material such as titanium or surgical grade stainless steel, such that one leg is entirely or partially formed from one material, and the other leg is entirely or partially formed from another material.

With reference to FIGS. 70-72, there are depicted further alternative embodiments of the surgical clip structures of the subject invention. With particular reference to FIG. 70, there is depicted a surgical clip 600a in the form of a generally U-shaped member. The clip 600a includes a generally V-shaped base 601 that is comprised of two base segments 601a and 601b which terminate at a base apex 601c. However, the base can be provided with a variety of alternative configurations, such as curvalinear or semi-circular, for facilitating use of the clip 600a with a suitable applicator such as that disclosed in my co-pending application Ser. No. 515,641, the disclosure of which is hereby incorporated by reference. The clip 600a includes a pair of opposed, elongated legs 602a and 604a which extend from a corresponding base arm 601a and 601b. the leg 602l is provided with a plurality of apertures 603a along substantially the entirety of its length that are dimensioned to interlockingly engage corresponding pin projections or spicules 603b extending outwardly from leg 604a toward leg 602a when the legs are interlockingly engaged in the manner described above in connection with the clip embodiments depicted in FIGS. 41 and 51. Clip distal end interlocking means such as hook end 605 and angled end 607 are provided at the distal, free ends of the legs 602a and 604a, respectively, to provide for clip distal end interlocking engagement prior to further leg relative displacement incident to securement of the clip in place in or along the body of a patient.

FIGS. 71 and 72 illustrate a further alternative aspect of the clip structures of the subject invention. With reference to FIG. 71, there is depicted a surgical clip 1600 that is configured as an integral structure comprised of a pair of generally opposed U-shaped members 1602 and 1604. Member 1602 is comprised of a pair of legs 1602a and 1602b that are connected to one another along a curvalinear distal end 1603 at the respective leg distal ends. Member 1604 is comprised of a pair of legs 1604a and 1604b that are connected to one another along a curvalinear distal end 1605. Legs 1602a and 1604a are joined to one another along a curvalinear base segment 1606, whereas legs 1602b and 1604b are joined along curvalinear base segment 1608. The opposing surfaces of the respective opposed leg pairs 1602a & 1604a and 1602b & 1604b are provided with suitable mutually engageable elements, such as apertures 603a provided along legs 1602a &1604a and spicules or spines 603 b provided along legs 1602b &1604b. The spines 603b and apertures 603a of corresponding leg pairs 1602a & 1604a and 1602b & 1604b are mutually engageable in the manner described above in connection with FIG. 70 to effect clip closure.

The clip 1600 is operable so as to aggregate tissue and organ structures and to close off various vessel structures. In use, the clip 1600 is manipulated relative to the respective structures so as to position the structure between the opposed members 1602 and 1604. The clip is closed in a manner analogous to the clips described above. Specifically, the respective distal ends of members 1602 and 1604 are interlockingly engageable upon engagement of corresponding spines and apertures 603b and 603a, respectively, so as to couple the distal ends of respective leg pairs 1602a & 1604a and 1602b &1604b, after which the respective leg pairs can be further coupled together by engagement of corresponding spines and apertures along the respective legs of the leg pairs so as to collapse generally transverse to the longitudinal axis separating the legs or in a progressive distal-to-proximal or proximal-to-distal manner. Preferably, the respective leg pairs are interengaged in the foregoing manner substantially simultaneously around the structure to be manipulated by the clip.

FIG. 72 depicts an alternative aspect of the double clip depicted in FIG. 71, in which the respective base segments 1606 and 1608 define outwardly-extending spices 1609 and 1611, respectively, which facilitate closure of the respective leg pairs 1602a &1604a and 1602b &1604b in the foregoing manner as well as for providing for cooperation with correspondingly-dimensioned components of clip applicators of the type disclosed in co-pending application Ser. No. 515,641. Clip distal end interlocking means of the type referenced above can optimally be provided along the distal ends 1603 and 1605 of the respective configurations of the clip 1600.

An applicator 1000 for applying the various double-leg suture tie devices of FIGS. 36A through 39 according to the present invention is illustrated in FIGS. 52 and 53. The applicator includes an array of three concentrically-arranged tubular members: an inner cartridge member 1010, an intermediate tubular member 1030, and an outer tubular member 1050. The inner cartridge 1010 houses a plurality of suture tie devices, such as the devices 300 depicted in FIG. 53, which are disposed in an end-to-end fashion and are spring-biased distally by the force exerted by a spring member 1018 mounted within the cartridge member 1010. The cartridge 1010 includes a tubular member 1012 having a cap 1020 (FIG. 52) at its proximal end 1014 and an open distal end 1016. The distal end 1016 of the tubular member is preferably configured with blunt edges and is arranged so as to be engageable by outlying curved arms 1036 and 1038 of the intermediate tubular member 1030 by means such as tethers 1017 and 1019 as shown in detail in FIG. 54. The spring member 1018 is mounted within the cartridge tubular member 1012 in compression between the cartridge cap 1020 and a pusher member 1022 mounted at the distal end of the spring member 1018. The pusher member 1022 includes a recess formed therein to receive the proximal end of the last (i.e., most proximally positioned) of the series of suture tie devices loaded within cartridge 1010.

The proximal end 1032 of the intermediate tubular member 1030 is secured to a collar 1034. Two or more expandable curved arms 1036 and 1036', 1038 and 1038' (FIGS. 52 and 55) are provided at the distal end of the tubular member 1030 and can be configured with blunt or sharp distal ends 1040 and 1040', 1042 and 1042', respectively. The intermediate tubular member 1030 is disposed between cartridge tubular member 1012 and the outer tubular member 1050, which has a proximal end 1052 secured to collar 1054 and a distal end that terminates at two or more fixed needles 1056 and 1058 (FIG. 53). The needles are preferably generally U-shaped in cross section and have a configuration which can vary in shape in accordance with the curvature of the legs of the suture tie devices, as illustrated in FIGS. 56 and 57 and the configuration of the distal ends of the suture tie device legs. The needles 1056 and 1058 terminate at sharp distal ends 1060 and 1062, respectively, which can "be configured so as to provide for tissue cutting and penetration in instances where the distal ends of the suture tie devices themselves are not configured with sharp, tissue penetrating edges. Alternatively, the distal ends 1060 and 1062 of the instrument 1000 can be configured as non-sharpened ends in instances where the suture tie devices to be applied by the instrument are provided with relatively sharp tissue penetrating distal ends.

With reference to FIG. 58, collapsible guides 1063 can be provided along the interior wall of the outer tubular member 1050 adjacent to the curved distal arms 1036 and 1038 (see FIGS. 52 and 54) of intermediate tubular member 1030. The guides 1063 extend distally toward the center of the tubular 1050 to direct the distal-most suture tie device to a loading position between the needles 1056 and 1058. After one of the suture tie devices has been loaded between the needles 1056 and 1058, the guides 1063 maintain the locking/tying member suture tie device at an appropriate position in order that the curved distal arms 1036 and 1038 can be manipulated so as to urge the locking/tying member in the distal direction to tie the suture loop.

The instrument 1000 can be provided with a generally U-shaped handle 1064 which has a distal arm 1066 secured to a distal collar 1054, a proximal arm 1068 secured to an intermediate collar 1034, and a spring biasing member 1067 extending between the arms 1066 and 1068. A curved spring member 1070 extends from intermediate collar 1034 to a proximal collar 1024 secured to cartridge tubular member 1012 and includes a finger grip 1072 that extends downwardly from the proximal collar 1024. A spacing adjustment mechanism 1074 can be provided to control the spacing between the distal ends 1040 and 1042 of the curved arms 1036 and 1038, respectively, between the generally closed position shown in FIG. 52 and the open position shown in FIG. 59. The spacing adjustment mechanism includes a rod 1076 having a distal end secured to the distal portion of the curved spring member 1070 adjacent to collar 1034. The proximal end of the rod 1076 extends through a passage 1071 formed in the proximal portion of the spring member 1070 and terminates at an adjustment switch 1078. The adjustment switch includes a knob 1080 pivotably mounted to the rod 1076 such that when the knob is in the vertical, upright position, the distal ends 1040 and 1042 of the tubular member 1030 are adjusted such that they are in the position shown in FIG. 52 to move that proximal end of the suture tie device. When switch 1078 is pivoted toward the distal end of the applicator such that the knob 1080 abuts the proximal portion of the spring member 1070, the distal ends 1040 and 1042 are urged apart to the position shown in FIG. 59 to permit passage of the locking/tying member distally past the distal ends to tie the suture loop.

An alternative spacing adjustment mechanism 1074', as shown in FIG. 60, can be provided to allow for more precise control for the spacing between the distal ends 1040 and 1042 at any position between the open and generally closed positions depicted in FIGS. 52 and 59 for the manipulation or severing of the proximal portion of the suture tie device loaded between the needles 1056 and 1058. The mechanism 1074' includes a threaded rod 1076' having a proximal portion which threadably receives a correspondingly-threaded adjustment nut 1078 and that terminates at its proximal end with a knob 1077. A mechanism 1081 for severing the proximally-extending portion of the suture tie device following suture loop formation can optionally be provided. The severing mechanism 1081, the operation of which is described below, includes a rod 1082 that is fixed at its distal end to the proximal arm 1068 of the U-shaped handle 1064 and that extends through a passage 1073 formed in the arm of the grip 1084 adjacent shoulder 1024.

In use, a cartridge 1010 having a plurality of serially-arranged suture tie devices is loaded in applicator 1000 through the open proximal end of the intermediate tubular member 1030. In order to position the distal-most suture tie device between the fixed needles 1056 and 1058, grip 1072 and proximal handle arm 1068 are squeezed together, thereby moving cartridge tubular member 1010 distally relative to the intermediate tubular member 1030 and causing distal end 1016 with its tethers 1017 and 1019 to open or expand distal arms 1036 and 1038 to the position depicted in FIG. 59. The spring bias of spring member 1018 mounted within the cartridge 1010 advances the distal-most suture tie device between needles 1056 and 1058 and beyond the expanded arms 1036 and 1038, such that the locking/tying member of the suture tie device is held in place by guides 1063. When the grip 1072 is released and the switch 1078 is in its upright (rest) position (FIG. 52), the curved arms 1036 and 1038 return to the position depicted in FIG. 52 due to the bias of the curved spring member 1070. With the suture tie device thus positioned between the needles 1056 and 1058, the tissue or organ structure can be sutured by penetrating the tissue with either one or both of the sharp distal ends 1060 and 1062 of the instrument needles 1056 and 1058 and/or the legs of the suture tie device in a conventional curved, suture needle-like fashion such that the sutured tissue is held between the needles 1056 and 1058. Following penetration of the tissue, arms 1066 and 1068 of the handle 1064 can be squeezed toward one another to move intermediate tubular member 1030 distally relative to outer tubular member 1050, thereby causing the ends 1040 and 1042 of curved arms 1036 and 1038 to push and advance the proximal end of the suture tie device distally to accomplish approximation, engagement or interlocking of the distal ends of the suture tie device. The tying function can be accomplished by pivoting switch 1078 completely to the left such that its knob 1080 abuts against the proximal portion of spring member 1070, thereby advancing tubular member 1012 slightly distally such that the arms 1036 and 1038 are expanded to the position depicted in FIG. 59, thereby allowing the proximal portion of the suture tie device to enter between the ends 1040 and 1042, which ends are positioned so as to push the locking/tying member in the distal direction upon distal extension of tubular member 1030 to diminish the size of the suture loop around the sutured tissue until the loop is ultimately tied with the desired level of tension.

Once the tying function is completed to a desired tension level, the protruding proximal portion of the suture tie device can optionally be severed at a desired length such that the tied loop remains intact. To accomplish this severing function, the space adjusting mechanism 1074' can be used to adjust the separation distance between the distal ends 1040 and 1042 such that they can be positioned in close surrounding proximity with the protruding proximal portion of the suture tie device; thereafter, the arms 1066 and 1068 of handle 1064 can be squeezed toward one another such that both the cartridge tubular member 1012 and the intermediate tubular member 1030 are moved distally together to move the distal ends 1040 and 1042 along the protruding proximal portion of the device until they reach the desired severing point. Thereafter, the grips 1072 and 1084 are squeezed together such that the tethers 1017 and 1019 of the tubular member 1012 pull the sharp distal ends 1040 and 1042 toward one another to sever the proximal portion of the suture tie device. After the severing function is completed, the handle 1064 is released, thereby allowing for the release of the tied suture tie device from the applicator 1000. As a plurality of suture tie devices can be supplied within the cartridge 1010, multiple suturing of organ and tissue structures can be accomplished without withdrawing the applicator from the body, thereby greatly simplifying and expediting suturing and minimizing the time during which the patient is under anesthesia.

Figure 61:
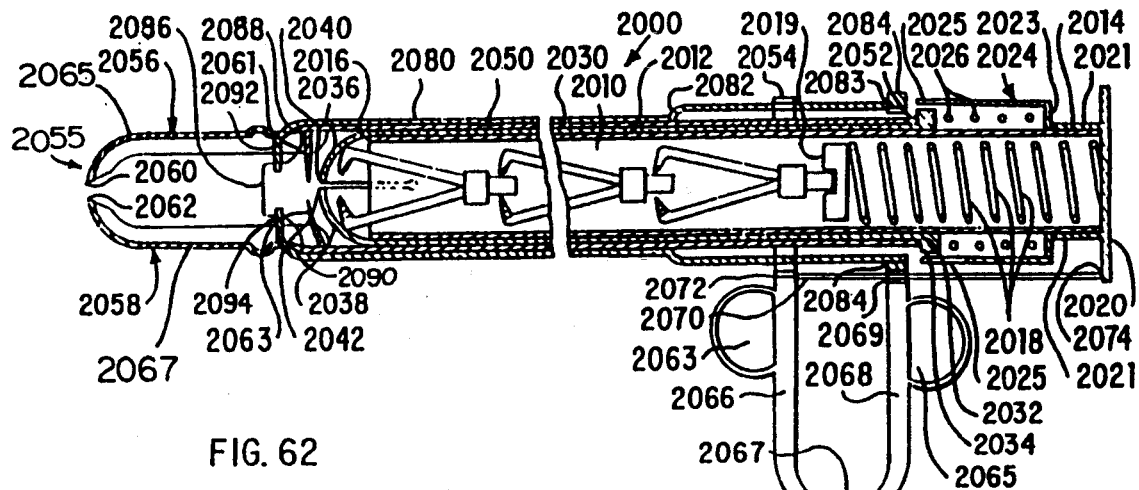
FIG. 61 is a sectional side view of an alternative suture tie device applicator for applying multiple leg suture tie devices as shown in FIGS. 36A through 41.

Another embodiment of a suture tie device applicator in accordance with the subject invention is depicted in FIG. 61. The applicator, designated in general by reference numeral 2000, includes a cartridge 2010 that is adapted to store a plurality of multiple leg suture tie devices of the type discussed above. The suture tie devices are disposed within the cartridge 2010 in an end-to-end serial arrangement and are spring-biased distally by a spring member 2018 that is mounted in compression between proximal end cap 2020 and pusher member 2019 in a manner substantially similar to that described above with respect to applicator 1000. The cap 2020 can be permanently affixed to the cartridge 2010, or it can be removably mounted thereto in a conventional manner, such as by mutual threaded engagement with the proximal end of the cartridge, to permit for cartridge reloading with additional and/or different types of multiple leg suture tie devices. The distal end 2016 of the cartridge is open-ended. The cap 2020 has a neck 2021 which extends distally and is arranged to abut against or to be fixed to the proximal portion 2023 of a hollow cylinder 2024. The cylinder 2024 houses a helical spring 2026 that is disposed between the cylinder 2024 and the cartridge 2010 and that is mounted in compression between a proximal collar 2034 of an outlying forcep tubular member 2050 and the proximal cylinder portion 2023. One or more slots 2025 is formed at the distal end of cylinder 2024 to allow for distal and proximal movement therein of a proximal collar 2084 of an outer tubular member 2080.

Figure 62:
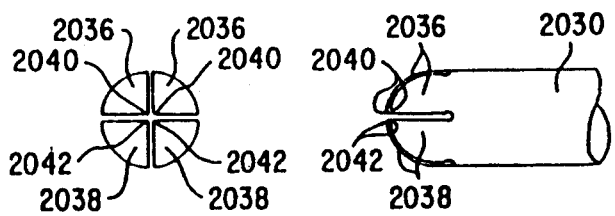
FIG. 62 is an end view of the distal end of the applicator of FIG. 61.
Figure 63:
FIG. 63 is a side view of the distal end of the applicator of FIG. 61.
Figures 64A, 64B, 64C:
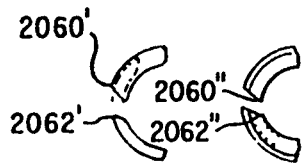
FIGS. 64A–64C and 66 are side views of the distal tips of the applicator forceps of FIG. 61.
Figure 66:
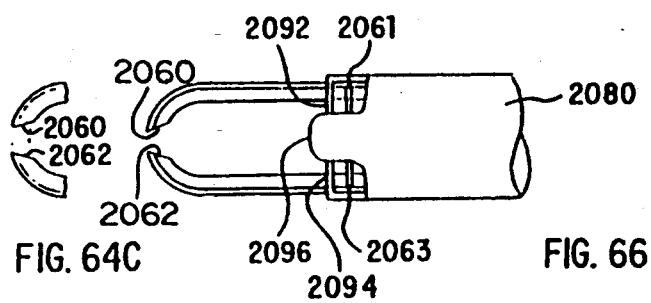
Figure 65:
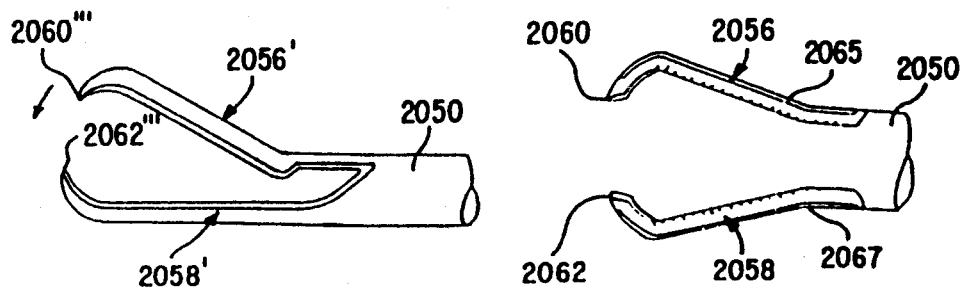
FIGS. 65 and 67 are side views of alternative forcep configurations.
Figure 67:
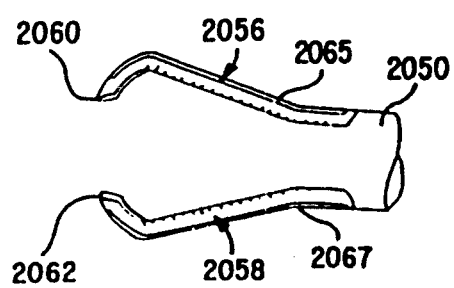

The proximal end 2032 of an intermediate tubular member 2030 is secured to collar 2034 and, at its distal end, is provided with at least one pair of curved, radially-expandable arms 2036 and 2038 which terminate at distal ends 2040 and 2042, as illustrated in side view in FIG. 62 and frontally in FIG. 63. The intermediate tubular member 2030 is disposed between the cartridge tubular member 2010 and the forcep tubular member 2050. The forcep tubular member 2050 includes a proximal end 2052 that is positioned adjacent to collar 2034 of intermediate tubular member 2030, a proximal portion that is secured to collar 2054, and a distal end which terminates at a forcep assembly 2055 that is comprised of at least two opposed forcep members 2056 and 2058. Each of the forcep members is preferably C-shaped or U-shaped in cross-section and is configured so as to accommodate the configuration of the suture tie devices utilized. At least one, and preferably both, of the forcep members terminates at a sharp distal end, such as ends 2060 and 2062 depicted in FIG. 61. As described with respect to applicator 1000, the length and configuration of the sharp ends 2060 and 2062 of the forceps can vary in accordance with the suture tie device used, thereby allowing for predetermined selection as to which one (or both) of the forcep ends functions as the tissue-penetrating member. In addition, the configuration of the distal ends may vary as shown in FIGS. 64A through 64C and 65, wherein the distal end 2062' is received within distal end 2060' (FIG. 64A), distal ends 2060" and 2062" meet at a slant (FIG. 64B), distal ends 2060 and 2062 meet at pointed tips (FIG. 64C), or in which distal end 2060''' is displaceable relative to fixed distal end 2062''' and received thereby. The configuration of the forceps 2056 and 2058 in their entirety can vary in accordance with the configuration of the suture tie device utilized, as shown in FIGS. 66 and 67. For example, suture tie devices of the present invention of the type comprising mutually displaceable legs, such as those depicted in FIGS. 36 through 39, can be utilized in connection with an applicator 2000 equipped with forceps 2056 and 2058 of FIG. 67, whereas the arrangement of movable and stationary legs of the suture tie devices of the present invention, such as those depicted in FIGS. 40 and 41, can be utilized in connection with an applicator 2000 equipped with an arrangement of movable and stationary forceps 2056' and 2058', respectively, as illustrated in FIG. 65. Referring once again to FIG. 61, protruding inwardly from the proximal portion of the forceps 2056 and 2058 is a pair of opposed pins 2061 and 2063 which are preferably configured with sharp distal tips to permit penetration and grasping of the proximal portion of the suture tie device when the forceps are in their closed position. The outer tubular member 2080 can optionally be provided with a slightly expanded proximal portion 2082 to limit the extent to which the applicator can be inserted within a portal or sleeve-like tubular member such as a trocar sleeve.

With reference to FIGS. 68A and 68B, a pair of opposed longitudinal slots 2087 and 2089 is disposed along the outward length of the forceps 2056 and 2058 to allow the distal and proximal movement of bilateral arms 2088 and 2090 of the outer tubular member 2080. The bilateral arms 2088 and 2090 protrude distally and terminate at holding members 2092 and 2094, which can vary in shape depending on the configuration of the locking/tying member of the suture tie device, and which prevent the locking/tying member from moving proximally as the forceps 2056 and 2058 are retracted proximally in the manner described below incident to suture tying. Also protruding from the distal end 2036 of the outer tubular member is a pair of opposed retaining members 2096 and 2098 which inhibit distal movement of the locking/tying member therepast.

The applicator 2000 includes a generally U-shaped handle 2064 for manipulating the various tubular members of the applicator 2000. The handle 2064 includes a distal arm 2066 secured to a collar 2054, a proximal arm 2068 secured to a collar 2084, a spring bias 2067 connecting the two arms 2066 and 2068, and ring handles 2063 and 2065 extending from the respective arms 2066 and 2068 to facilitate grasping of the handle. A rod 2070 secured at its distal end 2072 to distal arm 2066 extends through a passage 2069 formed in the proximal arm 2068 and is secured at its proximal end 2074 to cap 2020.

In use, a cartridge 2010 with a plurality of multiple leg suture tie devices serially arranged therein is loaded or pre-mounted within tubular member 2030 of the applicator 2000. In order to position the distal-most suture tie device into the forceps 2056 and 2058, ring handles 2063 and 2065 are spread apart, thereby moving forcep tubular member 2050 distally to open the inwardly-tensioned forceps and moving collar 2084 proximally through slots 2025 as it abuts and pushes collar 2034 proximally to move intermediate tubular member 2030 in the proximal direction. Upon movement of the handle arms in the aforedescribed manner, cap 2020 and cartridge tubular member 2012 are displaced distally by the rod 2070, ultimately causing blunt distal end 2016 of the cartridge tubular member 2010 to distally open or expand the curved arms 2036 and 2038 and allowing the spring bias within the cartridge to push the distal-most suture tie device into the forceps 2056 and 2058 past the expanded arms 2036 and 2038, as illustrated in FIG. 69. When the ring handles 2063 and 2065 are released, the curved arms 2036 and 2038 return to their normal (rest) position due to the bias of spring 2026. With the suture tie device positioned in the forceps, the tissue or organ structure can be sutured by penetrating the tissue with either or both sharp distal ends of the forceps and/or the suture tie device in a conventional suture needle-like fashion.

Following penetration of the tissue, ring handles 2063 and 2065 are squeezed toward one another, thereby moving forcep tubular member 2050 distally relative to outer tubular member 2080 to substantially or completely close the forceps such that their distal ends 2060 and 2062 approach or abut against one another to ensure the interlocking of the distal ends of the suture tie device loaded within the forceps 2056 and 2058. Once the forceps close together, the ends of pins 2061 and 2063 pierce and grasp the proximal portion of the suture tie device. After the distal ends of the forceps are displaced toward one another, the ring handles are squeezed further toward one another, thereby displacing the closed forceps proximally- Because the proximal portion of the suture tie device is engaged by the forceps pins, the proximal suture tie device portion is pulled proximally as well; simultaneously, the locking/tying member of the suture tie device is moved distally by the holding members 2092 and 2094 and the retaining members 2096 and 2098 of the outer tubular member 2080 to accomplish the tying function. Once the tying function is completed to a desired degree of suture knot tension, the handle 2067 is released, thereby allowing the tied suture tie device to be released from the applicator 2000. As a plurality of suture tie devices are supplied within the cartridge 2010, multiple suture suturing procedures can be accomplished without withdrawing the applicator 2000 from the suture site.

From the foregoing detailed description, it will be appreciated that the suture tie devices of the present invention allow tissue penetration and suture tying in a manner that will be more familiar to surgeons than that provided by known devices. Accordingly, the time normally required for suturing in both endoscopic and open surgery can be greatly reduced, in that no cumbersome, time-consuming manual tying of strands of suture material is required. The applicators of the present invention, all of which can be configured as reusable, partially-reusable or entirely disposable instruments, facilitate the use of the suture tie devices as described above and depicted in the accompanying drawings and allow the setting of multiple sutures at a surgical site without withdrawing the applicator from the body.

Inasmuch as the present invention is subject to various modifications and changes, the above description of preferred embodiments is intended to be exemplary only and not limiting. Further variations and changes which may occur to persons of ordinary skill in the surgical suturing art are specifically intended to be encompassed by the accompanying patent claims.

What is claimed is:

1. An adjsutably tensionalbe surgical clip, comprising:
    an elongated member comprised of at least one pair of first and second leg members, each of the leg members having a proximal portion and a distal portion having a tissue engaging portion which terminates at a distal end, a longitudinal channel means formed along at least a part of one of the leg members for engaging and retaining a corresponding part of the other leg member, the respective proximal portions of each leg member pair being pivotably connected to one another to permit relative displacement of the leg members, the distal portion of at least one leg member of each leg member pair being bendable relative to the distal portion of the other leg member of the pair to effect approximation of the leg member distal ends to close the clip prior to relative pivotable displacement of the leg members.

2. A surgical clip as recited in claim 1, wherein the elongated member is at least partially comprised of a bioabsorbable material.

3. A surgical clip as recited in claim 1, wherein the elongated member is at least partially comprised of titanium.

4. A surgical clip as recited in claim 1, wherein the elongated member is at least partially comprised of a surgical grade of stainless steel.

5. A surgical clip as recited in claim 1, wherein the first and second leg members are formed from different materials.

6. A surgical clip as recited in claim 1, wherein the distal end of said first leg member comprises receptacle means for receiving the distal end of the second leg member.

7. A suture tie device as recited in claim 6, wherein said channel means includes a channel defined in the second leg member that extend from said distal portion toward said proximal portion, said channel being dimensioned to receive therein the first leg member.

8. A surgical clip as recited in claim 7, wherein at least a portion of said leg member channel and at least a portion of the first leg member comprise mutually engageable interlocking means.

9. A surgical clip as recited in claim 8, wherein said interlocking means comprises a plurality of outwardly-extending ridges formed on one of the leg members and a plurality of inwardly-extending grooves formed on the other of the leg members.

10. A surgical clip as recited in claim 7, wherein said second leg member defining said channel is resiliently deformable to receive said first leg member.

11. A surgical clip as recited in claim 1, wherein the first and second leg members are formed as a unitary member.

12. A surgical as recited in claim 1, wherein the proximal portion of the first leg member comprises a sleeve member defining a lumen dimensioned to receivably retain the proximal portion of the second leg member.

13. A surgical clip as recited in claim 1, wherein at least one of the leg members has a substantially linear configuration prior to distal end bending.

14. A surgical clip as recited in claim 1, wherein the channel si resiliently deformable to receive the other leg member.

15. A surgical clip as recited in claim 1, wherein at least one of the leg members has a curved configuration prior to distal end bending.

16. A surgical clip as recited in either of claim 1, wherein said first and second legs are progressively displaceable toward one another from the distal end thereof toward a leg proxmal end.

17. A surgical clip as recited in either of claim 1 the legs members being progressively displaceable toward one another following clip closure from a proximal end thereof toward the leg distal ends.

18. A surgical clip as recited in claim 1, wherein the respective distal ends of the leg member distal portions comprise means for interlockingly engaging one another.

19. A surgical clip as recited in claim 1, wherein at least one leg member of the pair is predisposed along a distal end thereof so as to extend toward a distal end of the other leg of the leg pair.

20. An adjustably tensionable surgical clip, comprising:
    an elongated member comprised of at least one pair of first and second leg members, each of the leg members having a proximal portion and a distal portion having a tissue engaging portion which terminates at a distal end, at least one of the leg member including engaging and retaining means comprising a complementary arrangement of mutually engageable members formed along at least a section of each leg member, the mutually engageable members comprising a plurality of ridges formed on one leg member and a plurality of grooves formed along the other of the leg members, the grooves being dimensioned to retainably receive the plurality of ridges, the respective proximal portions of each leg member pair being pivotably connected to one another to permit relative displacement of the leg members, the distal portion of at leas tone leg member of each leg member pair being bendable relative to the distal portion of the other leg member of the pair to effect approximation of the leg member distal ends to close the clip prior to relative pivotable displacement of the leg members.

* * * * *